(12) United States Patent
Yoo et al.

(10) Patent No.: US 12,400,420 B2
(45) Date of Patent: Aug. 26, 2025

(54) MEDICAL IMAGING DEVICE AND MEDICAL IMAGE PROCESSING METHOD

(71) Applicant: LUNIT INC., Seoul (KR)

(72) Inventors: Dong Geun Yoo, Seoul (KR); Min Chul Kim, Seoul (KR); Hyo Eun Kim, Seongnam-si (KR); Hyun Jae Lee, Hwaseong-si (KR); Jae Hwan Lee, Seoul (KR); Hae Joon Kim, Seoul (KR)

(73) Assignee: LUNIT INC., Seoul (KR)

( * ) Notice: Subject to any disclaimer, the term of this patent is extended or adjusted under 35 U.S.C. 154(b) by 326 days.

(21) Appl. No.: 17/895,315

(22) Filed: Aug. 25, 2022

(65) Prior Publication Data

US 2022/0415013 A1 Dec. 29, 2022

Related U.S. Application Data

(63) Continuation of application No. PCT/KR2021/002426, filed on Feb. 25, 2021.

(30) Foreign Application Priority Data

Feb. 28, 2020 (KR) ........................ 10-2020-0025445

(51) Int. Cl.
*G06V 10/46* (2022.01)
*G06T 7/70* (2017.01)
(Continued)

(52) U.S. Cl.
CPC ................ *G06V 10/46* (2022.01); *G06T 7/70* (2017.01); *G06T 11/203* (2013.01); *G06V 10/25* (2022.01);
(Continued)

(58) Field of Classification Search
CPC ........ G06V 10/46; G06V 10/25; G06V 10/44; G06V 10/761; G06V 2201/07; G06T 7/70;
(Continued)

(56) References Cited

U.S. PATENT DOCUMENTS 10,497,157 B2 * 12/2019 Sevenster ............... G06T 11/60
2009/0248441 A1 10/2009 Okada
(Continued)

FOREIGN PATENT DOCUMENTS

CN 106529115 B * 10/2019 ............. A61B 5/743
JP H111755896 A * 7/1999 ............. G06F 17/50
(Continued)

OTHER PUBLICATIONS

"Albert Clerigues et. al., Acute Ischemic Stroke Lesion Core Segmentation in CT perfusion Images using Fully Convolutional Neural Networks, Dec. 2019, Computers in Biology and Medicine, vol. 115" (Year: 2019).*
(Continued)

*Primary Examiner* — Chineyere Wills-Burns
*Assistant Examiner* — Phuong Hau Cai
(74) *Attorney, Agent, or Firm* — Sughrue Mion, PLLC

(57) ABSTRACT

A method for operating a medical imaging device includes obtaining lesion information on at least one lesion detected from a medical image, determining a shape and a position of at least one contour corresponding to the at least one lesion based on the obtained lesion information, determining a position of at least one text region that includes a text indicating the lesion information on the at least one lesion in the medical image, and displaying the at least one contour and the text included in the at least one text region on the
(Continued)

medical image, based on the determined shape and position of the at least one contour and the determined position of the at least one text region.

16 Claims, 22 Drawing Sheets

(51) Int. Cl.
  *G06T 11/20* (2006.01)
  *G06V 10/25* (2022.01)
  *G06V 10/44* (2022.01)
  *G06V 10/74* (2022.01)

(52) U.S. Cl.
  CPC ............ *G06V 10/44* (2022.01); *G06V 10/761* (2022.01); *G06V 2201/07* (2022.01)

(58) Field of Classification Search
  CPC ....... G06T 11/203; A61B 6/463; A61B 6/502; A61B 6/468; A61B 8/463; A61B 8/468; A61B 6/5217; A61B 6/12; A61B 8/5223; G16H 30/40; G16H 50/70; G16H 30/20; G16H 50/20
  See application file for complete search history.

(56) References Cited

U.S. PATENT DOCUMENTS

| | | |
|---|---|---|
| 2011/0184291 A1 | 7/2011 | Okamura et al. |
| 2013/0343626 A1 | 12/2013 | Rico et al. |
| 2016/0334964 A1 | 11/2016 | Jeon et al. |
| 2017/0011516 A1 | 1/2017 | Snook et al. |
| 2017/0091949 A1 | 3/2017 | Akasaka et al. |

FOREIGN PATENT DOCUMENTS

| | | |
|---|---|---|
| JP | 2009-238037 A | 10/2009 |
| JP | 2011172918 A | 9/2011 |
| JP | 2015-138428 A | 7/2015 |
| JP | 2017505204 A | 2/2017 |
| JP | 2017-51591 A | 3/2017 |
| KR | 1020140070081 A | 6/2014 |
| KR | 102216697 B1 | 2/2021 |

OTHER PUBLICATIONS

"Xinjian Chen et. al., Medical Image Segmentation by Combining Graph Cuts and Oriented Active Appearance Models, Apr. 2012, vol. 21, Issue 4" (Year: 2012).*

Communication dated Apr. 30, 2025, issued in European Application No. 21 759 916.6.

* cited by examiner

```
Algorithm
410 ⎯ Given: C detected by a model from a CXR
      for i in {1, 2, ⋯, M − 1} do
  420 ⎯ $c_p \leftarrow R(i)$
  430 ⎯ $d_p \leftarrow D(c_p)$
         for j in {2, 3, ⋯, M} do
  440 ⎯ $c_q \leftarrow R(j)$
  450 ⎯ $d_q \leftarrow D(c_q)$
  460 ⎯ if $IoU(c_p, c_q) > MT_{d_q}$ and $S(c_q) < ST_{d_q}$ do
     470 ⎯ if $Sim(d_p, d_q) == 1$ or $CoOcc(d_p, d_q) == 0$ do
        480 ⎯ Remove $c_q$ from C
               end
            end
         end
490 ⎯ end
      Visualize C
```

FIG. 4

MEDICAL IMAGING DEVICE AND MEDICAL IMAGE PROCESSING METHOD

CROSS-REFERENCE TO RELATED APPLICATION

The present application is a continuation of International Patent Application No. PCT/KR2021/002426, filed Feb. 25, 2021, which is based upon and claims the benefit of priority to Korean Patent Application No. 10-2020-0025445, filed on Feb. 28, 2020. The disclosures of the above-listed applications are hereby incorporated by reference herein in their entirety.

TECHNICAL FIELD

The present disclosure relates to a device and a method for obtaining lesion information from a medical image and displaying the lesion information on a medical image.

BACKGROUND

As technologies such as big data or artificial intelligence develop, the reliability of technologies for automatically detecting lesions from medical images is increasing. Accordingly, the medical device can detect a plurality of lesions from a medical image. However, if all information on a plurality of detected lesions is displayed on one medical image, there can be excessive information displayed on the medical image. Too much information displayed on the medical image can obstruct the original image, and it will take a long time for a medical practitioner to diagnose with the information displayed on a plurality of lesions. In addition, the medical practitioner may miss some of the information displayed on the plurality of lesions.

Therefore, there is a need for a technique for effectively displaying the lesion on the image.

SUMMARY

In order to address one or more problems (e.g., the problems described above and/or other problems not explicitly described herein), the present disclosure provides a method for medical image processing, a non-transitory computer-readable recording medium storing instructions for medical image processing, and a medical imaging device (system) for medical image processing.

A method for operating a medical imaging device may include obtaining lesion information on at least one lesion included in a medical image, generating at least one contour corresponding to the at least one lesion in the medical image based on the obtained lesion information, and outputting at least one contour generated on the medical image.

The generating the at least one contour of the method for operating the medical imaging device may include generating a contour based on at least one of: information related to an overlapping lesion region between a plurality of lesions included in the medical image; or information related to relevance between the plurality of lesions, based on the obtained lesion information.

The generating the at least one contour of the method for operating the medical imaging device may include determining a size of an overlapping region between the region of the first lesion and the region of the second lesion, based on the first lesion information and the second lesion information included in the plurality of lesions, determining information related to probability of presence of a second lesion in the medical image based on the second lesion information, and generating at least one contour surrounding the first lesion, if the size of the overlapping region is greater than the first threshold value and information related to the probability of presence of the second lesion in the medical image is less than the second threshold value.

The generating the at least one contour of the method for operating the medical imaging device may include determining presence of pathological similarity between the first lesion and the second lesion, determining presence of coexistence between the first lesion and the second lesion for the same region, if the presence of similarity indicates that the first lesion and the second lesion are similar to each other, or if the presence of coexistence indicates that the first lesion and the second lesion cannot coexist with each other, generating at least one contour surrounding the first lesion, and not generating at least one contour surrounding the second lesion.

The method for operating the medical imaging device may further include arranging the plurality of lesion information in the order of higher probability of presence in the medical image, based on the plurality of lesion information, in which the first lesion has a higher probability of presence in the medical image than the second lesion.

The outputting the at least one contour of the method for operating the medical imaging device may include determining first candidate arrow information for a plurality of first candidate arrows pointing to a first contour of the at least one contour, determining an arrow-text region outside the first contour, determining, in the arrow-text region, a contact region where one side of a text box corresponding to the plurality of first candidate arrows and displaying lesion information for the first contour meets one end of a plurality of first candidate arrows included in the first candidate arrow information, generating, based on the determined contact region, at least one set of arrows for displayable positions of the text box for the first contour and the arrows, obtaining a score for each of the at least one set of arrows and selecting one of the at least one set of arrows based on the obtained score, and outputting an arrow and text in the text box together with the at least one contour, based on the selected one set of arrows.

The determining the first candidate arrow information of the method for operating the medical imaging device may include, if the first text box for the first contour overlaps with the second text box for the second contour or the second contour, moving the start point or end point of the candidate arrow included in the first candidate arrow information such that the first text box does not overlap with the second text box or the second contour, so as to obtain modified first candidate arrow information, and the generating the at least one set of arrows may include generating the at least one set of arrows based on the modified first candidate arrow information.

The method for operating the medical imaging device may further include determining second candidate arrow information for a plurality of second candidate arrows pointing to a second contour of the at least one contour, the determining the first candidate arrow information may include moving a start point or an end point of one of the plurality of first candidate arrows to obtain modified first candidate arrow information such that one of the plurality of first candidate arrows and one of the plurality of second candidate arrows do not cross each other, and the generating the at least one set of arrows may include generating the at least one set of arrows based on the modified first candidate arrow information.

The determining the first candidate arrow information of the method for operating the medical imaging device may include obtaining an intersection point of the first contour and a second contour of the at least one contour, obtaining a first contact point where the first contour and one of the plurality of first candidate arrows meet, modifying the position of a start point or an end point of one of the plurality of first candidate arrows such that the first contact point is at a distance away from the intersection point by a threshold value or more, so as to obtain modified first candidate arrow information, and the generating the at least one set of arrows may include generating the at least one set of arrows based on the modified first candidate arrow information.

The arrow-text region of the method for operating the medical imaging device may not be in contact with the first contour, but have a ring shape surrounding the first contour.

The score of the method for operating the medical imaging device may increase as the distance between at least one text box corresponding to the at least one contour increases, or may increase as the length of the at least one arrow corresponding to the at least one contour decreases, or may increase as the distance between the intersection point of the two contours included in the at least one contour and the contact point between the at least one contour and the at least one arrow increases.

The generating the at least one contour of the method for operating the medical imaging device may include determining the position and the shape of at least one contour based on the obtained lesion information.

The determining the position and the shape of the at least one contour of the method for operating the medical imaging device may include obtaining probability that each pixel in the medical image is included in the region of at least one lesion, based on the lesion information, and determining a thickness of the at least one contour based on the probability of inclusion in the region of the at least one lesion.

A medical imaging device may include a processor and a memory, and the processor may be configured to obtain lesion information on at least one lesion included in a medical image according to the instructions included in the memory, generate least one contour corresponding to at least one lesion in the medical image based on the obtained lesion information, and output at least one contour generated on the medical image.

The processor of the medical imaging device may be configured to, according to the instructions included in the memory, generate a contour based on at least one of: information related to an overlapping lesion region between a plurality of lesions included in the medical image; or information related to relevance between the plurality of lesions, based on the obtained lesion information.

The processor of the medical imaging device may be configured to, according to the instructions included in the memory, determine size of an overlapping region between the region of the first lesion and the region of the second lesion, based on the first lesion information and the second lesion information included in the plurality of lesions, determine information related to probability of presence of a second lesion in the medical image based on the second lesion information, and generating at least one contour surrounding the first lesion, if the size of the overlapping region is greater than the first threshold value and information related to the probability of presence of the second lesion in the medical image is less than the second threshold value.

The processor of the medical imaging device may be configured to, according to the instructions included in the memory, determine presence of pathological similarity between the first lesion and the second lesion, determine presence of coexistence between the first lesion and the second lesion for the same region, and if the presence of similarity indicates that the first lesion and the second lesion are similar to each other, or if the presence of coexistence indicates that the first lesion and the second lesion cannot coexist with each other, generating at least one contour surrounding the first lesion, and not generating at least one contour surrounding the second lesion.

The processor of the medical imaging device may be configured to, according to the instructions included in the memory, arrange the plurality of lesion information in the order of higher probability of presence in the medical image, based on the plurality of lesion information, in which the first lesion has a higher probability of presence in the medical image than the second lesion.

The processor of the medical imaging device may be configured to, according to the instructions included in the memory, determine first candidate arrow information for a plurality of first candidate arrows pointing to a first contour of the at least one contour, determine an arrow-text region outside the first contour, determine, in the arrow-text region, a contact region where one side of a text box corresponding to the plurality of first candidate arrows and displaying lesion information for the first contour meets one end of a plurality of first candidate arrows included in the first candidate arrow information, generate, based on the determined contact region, at least one set of arrows for displayable positions of the text box for the first contour and the arrows, obtain a score for each of the at least one set of arrows, and select one of the at least one set of arrows based on the obtained score, and output an arrow and text in the text box together with the at least one contour, based on the selected one set of arrows.

The processor of the medical imaging device may be configured to, according to the instructions included in the memory, if the first text box for the first contour overlaps with the second text box for the second contour or the second contour, move the start point or end point of the candidate arrow included in the first candidate arrow information such that the first text box does not overlap with the second text box or the second contour, so as to obtain modified first candidate arrow information, and generate the at least one set of arrows based on the modified first candidate arrow information.

The processor of the medical imaging device may be configured to, according to the instructions included in the memory, determine second candidate arrow information for a plurality of second candidate arrows pointing to a second contour of the at least one contour, moving a start point or an end point of one of the plurality of first candidate arrows to obtain modified first candidate arrow information such that one of the plurality of first candidate arrows and one of the plurality of second candidate arrows do not cross each other, and generate the at least one set of arrows based on the modified first candidate arrow information.

The processor of the medical imaging device may be configured to, according to the instructions included in the memory, obtain an intersection point of the first contour and a second contour of the at least one contour, obtain a first contact point where the first contour and one of the plurality of first candidate arrows meet, modify the position of a start point or an end point of one of the plurality of first candidate arrows such that the first contact point is at a distance away from the intersection point by a threshold value or more, so as to obtain modified first candidate arrow information, and generate the at least one set of arrows based on the modified first candidate arrow information.

The arrow-text region of the medical imaging device may not be in contact with the first contour, but have a ring shape surrounding the first contour.

The score of the medical imaging device may increase as the distance between at least one text box corresponding to the at least one contour increases, or may increase as the length of the at least one arrow corresponding to the at least one contour decreases, or may increase as the distance between the intersection point of the two contours included in the at least one contour and the contact point between the at least one contour and the at least one arrow increases.

The processor of the medical imaging device may be configured to, according to the instructions included in the memory, determine the position and the shape of at least one contour based on the obtained lesion information.

The processor of the medical imaging device may be configured to, according to the instructions included in the memory, obtain probability that each pixel in the medical image is included in the region of at least one lesion, based on the lesion information, and determine a thickness of the at least one contour based on the probability of inclusion in the region of the at least one lesion.

A method for operating a medical imaging device may include obtaining lesion information on at least one lesion detected from a medical image, determining a shape and a position of at least one contour corresponding to the at least one lesion based on the obtained lesion information, determining a position of at least one text region that includes a text indicating the lesion information on the at least one lesion in the medical image, and displaying the at least one contour and the text included in the at least one text region on the medical image, based on the determined shape and position of the at least one contour and the determined position of the at least one text region.

The determining the position of the at least one text region may include determining the position of the at least one text region based on at least one of: a distance between the at least one contour and the at least one text region; or presence of overlap between the at least one contour and the at least one text region.

The obtaining may include obtaining lesion information on a plurality of lesions detected from the medical image. The determining the shape and the position of the at least one contour may include determining some of the plurality of lesions to be displayed on the medical image, and determining the shape and a position of at least one contour for the determined some lesions. The determining the position of the at least one text region may include determining a position of at least one text region including the lesion information on the determined some lesions.

The determining the some lesions may include identifying any of the plurality of lesions that has an overlapping lesion region, and determining some of the plurality of lesions based on at least one of: a size of the overlapping region between overlapping lesions; probability that each of the overlapping lesions is a lesion; relevance between overlapping lesions; or probability of presence of some of the overlapping lesions in one medical image.

The method may further include generating at least one arrow pointing to the at least one contour. The displaying may include displaying the generated at least one arrow on the medical image to connect the at least one contour and the at least one text region.

The obtaining may include obtaining lesion information on a plurality of lesions detected from the medical image. The generating the arrow may include generating an arrow for each of the plurality of lesions. The displaying the generated arrow on the medical image may include displaying the arrows for each of the plurality of lesions on the medical image such that the generated arrows for each of the plurality of lesions do not cross each other.

The obtaining may include obtaining lesion information on a plurality of lesions detected from the medical image. The generating the arrow may include generating an arrow for each of the plurality of lesions. The displaying the generated arrow on the medical image may include displaying arrows for each of the plurality of lesions on the medical image such that the generated arrows for each of the plurality of lesions do not cross a contour corresponding to each of the plurality of lesions.

The displaying the generated arrow on the medical image may include determining at least one contact region in which the generated arrow is in contact with the at least one contour, and displaying the generated at least one arrow as being connected to the at least one contact region.

The determining the at least one contact region may include determining, from a plurality of contact regions contacting the at least one contour, the at least one contact region based on a distance between the plurality of contact regions.

The at least one text region may include a plurality of text regions, and the determining the position of the at least one text region may include determining a position of each of the plurality of text regions based on a distance between the plurality of text regions.

An electronic device may include a memory storing one or more instructions, and a processor configured to execute the stored one or more instructions to obtain lesion information on at least one lesion detected from a medical image; determine a shape and a position of a contour corresponding to the at least one lesion based on the obtained lesion information, determine a position of at least one text region that includes a text indicating the lesion information on the at least one lesion in the medical image, and display the at least one contour and the text included in the at least one text region on the medical image based on the determined shape and position of the at least one contour and the determined position of the at least one text region.

The processor may be further configured to determine the position of the at least one text region based on at least one of: a distance between the at least one contour and the at least one text region; or presence of overlap between the at least one contour and the at least one text region.

The processor may be further configured to obtain lesion information on a plurality of lesions detected from the medical image, determine some of the plurality of lesions to be displayed on the medical image, determine the shape and position of at least one contour for the determined some lesions, and determine a position of at least one text region including the lesion information on the determined some lesions.

The processor may be further configured to identify any of the plurality of lesions that has an overlapping lesion region, and determine some of the plurality of lesions based on at least one of: a size of the overlapping region between overlapping lesions; probability that each of the overlapping lesions is a lesion; relevance between overlapping lesions; or probability of presence of some of the overlapping lesions in one medical image.

The processor may be further configured to generate at least one arrow pointing to the at least one contour, and display the generated at least one arrow on the medical image to connect the at least one contour and the at least one text region.

The processor may be further configured to obtain lesion information on a plurality of lesions detected from the medical image, generate an arrow for each of the plurality of lesions, and display arrows for each of the plurality of lesions on the medical image such that the generated arrows for each of the plurality of lesions do not cross each other.

The processor may be further configured to obtain lesion information on a plurality of lesions detected from the medical image, generate an arrow for each of the plurality of lesions, and display arrows for each of the plurality of lesions on the medical image such that the generated arrows for each of the plurality of lesions do not cross a contour corresponding to each of the plurality of lesions.

The processor may be further configured to determine at least one contact region in which the generated arrow is in contact with the at least one contour, and display the generated arrow as being connected to the at least one contact region.

The processor may be further configured to determine, from a plurality of contact regions contacting the at least one contour, the at least one contact region based on a distance between the plurality of contact regions.

The at least one text region may include a plurality of text regions, and the processor may be further configured to determine a position of each of the plurality of text regions based on a distance between the plurality of text regions.

In addition, a program for implementing the method for operating the medical imaging device as described above may be recorded in a computer readable recording medium.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIG. 4 illustrates pseudo-code of a method for operating a medical imaging device.

DETAILED DESCRIPTION

Figure 1:
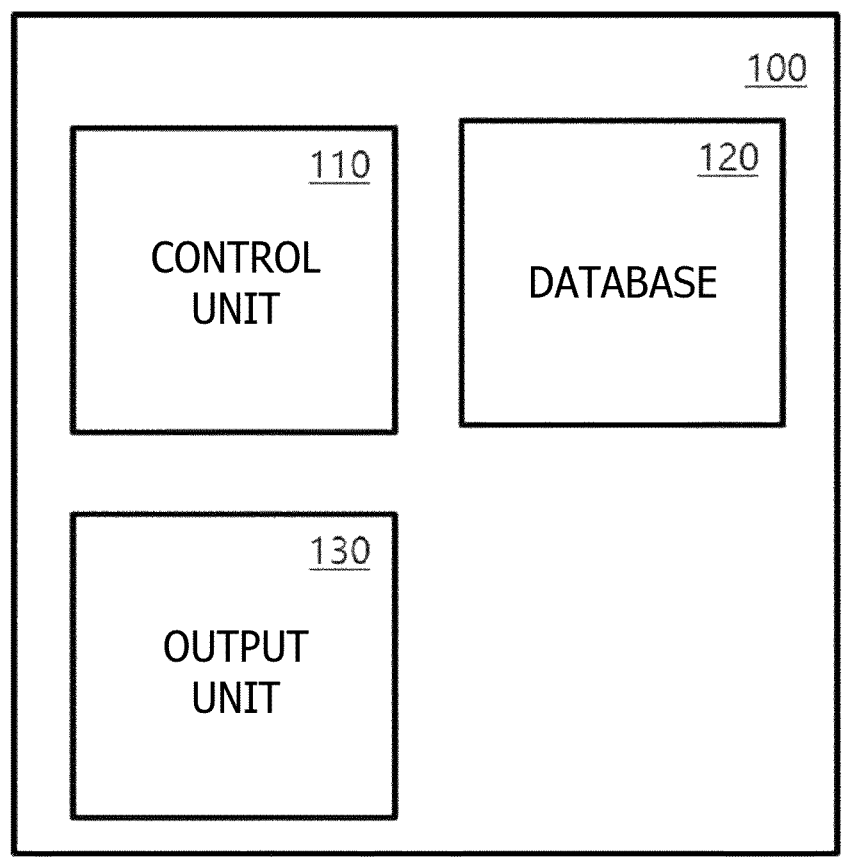
FIG. 1 illustrates a medical imaging device.

Advantages and features of the disclosed examples and methods of accomplishing the same will be apparent by referring to examples described below in connection with the accompanying drawings. However, the present disclosure is not limited to the examples disclosed below, and may be implemented in various different forms, and the examples are merely provided to make the present disclosure complete, and to fully disclose the scope of the invention to those skilled in the art to which the present disclosure pertains.

The terms used herein will be briefly described prior to describing the disclosed embodiment(s) in detail.

The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the embodiment(s). Therefore, the terms used in the present disclosure should be defined based on the meaning of the terms and the overall content of the present disclosure rather than a simple name of each of the terms.

As used herein, the singular forms 'a,' 'an,' and 'the' are intended to include the plural forms as well, unless the context clearly indicates the singular forms. Further, the plural forms are intended to include the singular forms as well, unless the context clearly indicates the plural forms.

Further, throughout the description, when a portion is stated as "comprising (including)" a component, it intends to mean that the portion may additionally comprise (or include or have) another component, rather than excluding the same, unless specified to the contrary.

Furthermore, the term "unit" used herein denotes a software or hardware component, and the "unit" performs certain roles. However, the meaning of the "unit" not limited to software or hardware. The "unit" may be configured to be in an addressable storage medium, or may be configured to reproduce one or more processors. Accordingly, as an example, the "unit" includes elements such as software elements, object-oriented software elements, class elements, and task elements, processes, functions, attributes, procedures, subroutines, program code segments, drivers, firmware, micro-codes, circuits, data, database, data structures, tables, arrays, and variables. Furthermore, functions provided in the components and the "units" may be combined into a smaller number of components and "units", or further divided into additional components and "units".

The "unit" may be implemented as a processor and a memory. The term "processor" should be interpreted broadly to encompass a general-purpose processor, a central processing unit (CPU), a microprocessor, a digital signal processor (DSP), a controller, a microcontroller, a state machine, and the like. Under some circumstances, a "processor" may refer to an application-specific integrated circuit (ASIC), a programmable logic device (PLD), a field-programmable gate array (FPGA), and the like. The term "processor" may refer to a combination of processing devices, e.g., a combination of a DSP and a microprocessor, a plurality of microprocessors, one or more microprocessors in conjunction with a DSP core, or a combination of any other such configuration.

The term "memory" should be interpreted broadly to encompass any electronic component capable of storing electronic information. The term "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and the like. The memory is said to be in electronic communication with a processor if the processor can read information from and/or write information to the memory. The memory integrated with the processor is in electronic communication with the processor.

Hereinafter, examples will be fully described with reference to the accompanying drawings in such a way that those skilled in the art can easily carry out the examples. Further, in order to clearly illustrate the present disclosure, parts not related to the description are omitted in the drawings.

FIG. 1 illustrates a medical imaging device.

A medical imaging device 100 may include a control unit 110, a database 120, and an output unit 130. The control unit 110 may include at least one processor and at least one memory. The processor may execute instructions stored in the memory.

The database 120 may store various data. For example, the database 120 may store at least one of a medical image, an analysis result of a medical practitioner, and an analysis result of a medical analysis device. In addition, the database 120 may include a medical image analysis model for analyzing a medical image. The medical image analysis model may be a rule-based model or a machine learning model.

The output unit 130 may include at least one of an image output unit and a sound output unit. The output unit 130 may be controlled by the control unit 110. The output unit 130 may output at least one of a medical image and an analysis result.

Hereinafter, the operation of the medical imaging device 100 will be described in more detail.

Figure 2:
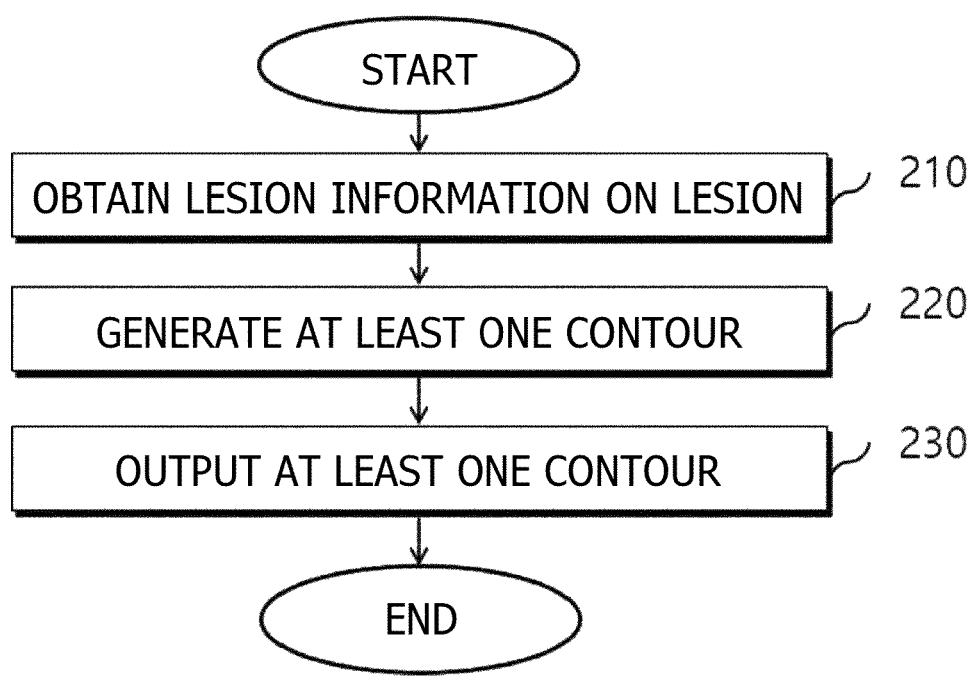
FIG. 2 is a flowchart illustrating an operation of a medical imaging device.

FIG. 2 is a flowchart illustrating an operation of the medical imaging device.

The medical imaging device 100 may perform obtaining (210) lesion information on at least one lesion included in the medical image. The medical image may be an image obtained by capturing a part of the patient's body. The medical image may be an image captured by various medical imaging devices. For example, the medical image may be one of CT, MRI, X-RAY, mammography, or ultrasound image. The medical image may be received from the database 120. In addition, the medical image may be received from an external device. For example, the medical image may be received from an external medical imaging device other than the medical imaging device 100.

The lesion information may be information on a lesion included in the medical image. The lesion information may be information on a lesion that is automatically analyzed and detected by the medical image analysis apparatus. However, aspects are not limited thereto, and the lesion information may be an analysis result by a medical practitioner.

The medical imaging device 100 may receive the lesion information from an external device or from the database 120 of the medical imaging device 100. In addition, the medical imaging device 100 may analyze the medical image using self-analysis tool to obtain lesion information. The self-analysis tool may be a rule-based model or a machine learning model for detecting lesions. For example, the self-analysis tool may include a medical image analysis model trained based on machine learning.

The lesion information may include at least one of information on the type of the lesion, information on the position of the lesion, information on the probability of presence of the lesion in a medical image, information on the shape of the lesion, information on the size of the lesion, and information on the region of the lesion.

The information on the type of the lesion may include at least one of a name of the lesion or classification information of the lesion. The information on the type of the lesion may be information on diagnosis by a medical practitioner, or information on diagnosis based on a self-analysis tool. As described above, the medical image analysis apparatus may obtain information on the type of the lesion from the medical image based on rule base or a machine learning model.

The position information of the lesion may indicate at least one point having the highest probability of presence of the lesion in the medical image. The position information of the lesion may be expressed as at least one coordinate value. The position information of the lesion may be a coordinate value of a pixel in which the lesion is positioned in the medical image. If the lesion occupies a partial region of the medical image, the position information of the lesion may be expressed as a plurality of coordinate values. In addition, the position information of the lesion may include coordinate values of one lesion point and radius information from the lesion point. However, aspects are not limited thereto, and position information of the lesion may be expressed in various ways.

The information on the probability of presence of the lesion in the medical image represents the probability of presence of the lesion in a part of the patient's body corresponding to the medical image, based on the medical image. The medical image analysis apparatus may detect a lesion present in the medical image by using a rule base or a machine learning model. In addition, the medical image analysis apparatus may also predict the probability of presence of the corresponding lesion in the medical image based on a rule base or a machine learning model. The information on the probability of presence of the lesion in the medical image may include probability value corresponding to each pixel included in the medical image. The information on the probability of presence of the lesion in the medical image may include probability value corresponding to a specific region of the medical image. In this case, the specific region is a region included in the medical image and may be an image that is smaller than or same as the medical image. The probability value corresponding to the specific region of the medical image may be obtained by the medical image analysis apparatus or may be received by a medical practitioner.

In addition, the medical imaging device 100 may determine probability value corresponding to a specific region based on probability value corresponding to a pixel included in the specific region. For example, the medical imaging device 100 may obtain a representative probability value corresponding to the specific region, using a maximum value, an average value, a median value, or a minimum value of the probability values of pixels included in the specific region. A medical practitioner may lower the probability of incorrect diagnosis by diagnosing based on the information on the probability.

The information on the shape of the lesion may indicate information related to the shape of the lesion. The information on the shape of the lesion may be information related to the shape of the outline of the lesion. The information on the shape of the lesion may have a circular, oval, or atypical shape. The information on the shape of the lesion may be determined by a diagnosis of a medical practitioner. In addition, the medical image analysis apparatus may obtain lesion shape information based on a rule base or a machine learning model.

The size information of the lesion is information on the size of the lesion, and may be the number of pixels included in the lesion region in the medical image. In addition, the size information of the lesion may be a horizontal length or a vertical length of the lesion in the medical image. In addition, the size information of the lesion may be the area of the lesion region in the medical image. The size information of the lesion may indicate the number of pixels included in the lesion region. In addition, the size information of the lesion may indicate a radius. That is, an inner region of a circle based on the central point and a radius of the lesion may represent the lesion region.

The region information of the lesion may indicate a region having a high probability of presence of the lesion in the medical image. The medical imaging device 100 may receive the region information of the lesion from a medical practitioner. In addition, the medical imaging device 100 may automatically obtain the region information of the lesion based on a rule base or a machine learning model. The medical imaging device 100 may calculate the probability of presence of the lesion for each pixel of the medical image. Alternatively, the medical imaging device 100 may calculate the probability of presence of the lesion for a pixel group. For example, the pixel group may include a plurality of pixels. The pixel group may represent a predetermined region in a medical image. The medical imaging device 100 may also calculate the probability of presence of the lesion for the pixel group. The medical imaging device 100 may determine that the pixel is included in the region of the lesion, if the probability of presence of the lesion in the pixel is equal to or greater than a threshold value. That is, the probability of presence of the lesion in the pixels included in the lesion region may be equal to or greater than the threshold value. The threshold value may be predetermined information.

The medical imaging device 100 may perform generating (220) at least one contour corresponding to at least one lesion in the medical image, based on the obtained lesion information.

The contour may indicate either the position or the shape of the lesion. The medical imaging device 100 may display at least one lesion with respect to one medical image. The plurality of lesions may have different positions and shapes. The medical imaging device 100 may obtain the position and the shape of at least one lesion based on the lesion information. The medical imaging device 100 may reflect the position and the shape of each lesion to generate a contour. That is, the medical imaging device 100 may determine the position and the shape of at least one contour based on the obtained lesion information. That is, the position of the contour may be determined based on the position of the lesion included in the lesion information of the medical imaging device 100. In addition, the medical imaging device 100 may determine the shape of the contour based on the shape of the lesion included in the lesion information.

The position of the contour may correspond to lesion position information included in the lesion information. The medical imaging device 100 may determine the shape of the contour based on the lesion information. The medical imaging device 100 may determine the contour by the following process.

More specifically, the medical imaging device 100 may determine the contour based on the outline of the lesion region included in the lesion information. As already described, the medical imaging device 100 may determine that the pixel is included in the region of the lesion, if the probability of presence of the lesion in the pixel is equal to or greater than the threshold value. That is, the probability of presence of the lesion in pixels within the lesion region may be equal to or greater than the threshold value. The medical imaging device 100 may determine, as a contour, the contour of the lesion region included in the lesion information. The contour may surround the lesion region.

In addition, the medical imaging device 100 may enlarge the contour of the lesion region in A times to obtain a contour including the lesion, where "A" may be a real number greater than 1. That is, the contour may be equal to or greater than the lesion region. Enlarging the contour of the lesion region in A times may mean that the horizontal length of the lesion region becomes A times as large and the vertical length becomes A times as large. Therefore, the area inside the contour may be $A^2$ times the area of the lesion region.

In addition, the medical imaging device 100 may determine, as a contour, a polygon, an oval, or a circle including the lesion region included in the lesion information. A medical practitioner may intensively observe around the contour, which is a part of the medical image, and finally, may easily determine whether or not a lesion is present inside the contour.

The shape of the contour may further include a thickness of the line of the contour. The medical imaging device 100 may obtain the thickness of the contour line based on the lesion information. For example, the medical imaging device 100 may obtain probability that each pixel in the medical image is included in the region of at least one lesion based on the lesion information. In addition, the medical imaging device 100 may determine the thickness of the at least one contour based on probability that a pixel included in the contour is included in the region of the at least one lesion. For example, the thickness of the contour may be increased as the probability increases.

The medical imaging device 100 may obtain probability that each pixel included in the medical image is included in the lesion. In addition, the medical imaging device 100 may determine, as a contour, a group of pixels having probability of inclusion in the lesion, that is equal to a threshold value. Since the probability of inclusion in the lesion is discontinuous, there may not be a value equal to the threshold value. In this case, if the probability corresponding to one of the two adjacent pixels is greater than the threshold value and the probability corresponding to the other one is less than the threshold value, one of the two adjacent pixels may be included in the contour. The probability that the pixel inside the contour is included in the lesion region may be greater than the threshold value. In this case, the threshold value may be a predetermined value.

In addition, the medical imaging device 100 may determine, as a contour, a group of pixels having probability of inclusion in the lesion, that is within a threshold range. The threshold range may be so narrow that the group of pixels may look like a line. The probability that the pixel inside the contour is included in the lesion region may be greater than a minimum value of the threshold range. In this case, the threshold range may be a predetermined range.

The configuration in which the medical imaging device 100 generates one contour on one lesion has been described above. If a plurality of lesions are present in the medical image, the medical imaging device 100 may generate a plurality of contours corresponding to the plurality of lesions. This will be described by referring to FIG. 3.

Figure 3:
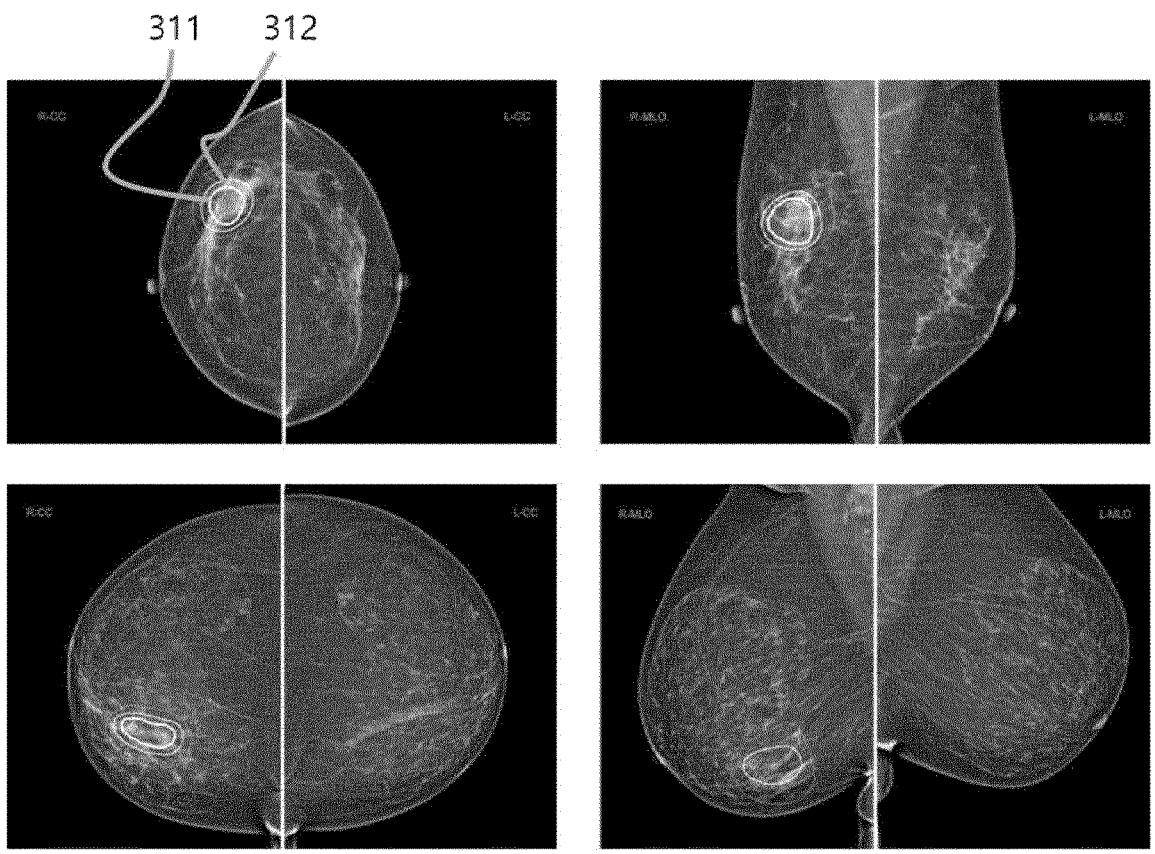
FIG. 3 illustrates a medical image.

FIG. 3 illustrates a medical image.

In addition, the medical imaging device 100 may generate at least one contour for one lesion included in the medical image. The medical imaging device 100 may generate at least one contour such as a contour line for one lesion. Probability that a pixel inside one of the plurality of lines included in the contour line is included in the lesion region may be greater than a threshold value.

Referring to FIG. 3, the medical image may include a first contour line 311 and a second contour line 312 for one lesion. The probability that the pixel included in the inner region of the first contour line 311 is included in the lesion region may be equal to or greater than the first threshold value. The probability that the pixel included in the inner region of the second contour line 312 is included in the lesion region may be equal to or greater than the second threshold value. The probability that pixels included in the inner region of the second contour line 312 and the outer region of the first contour line 311 are included in the lesion region may be lower than the first threshold value and equal to or greater than the second threshold value. In this example, the first threshold value and the second threshold value may be predetermined values. The first threshold value may be greater than the second threshold value.

The medical imaging device 100 may generate a thicker contour line as the probability that the pixel inside the contour line is included in the lesion region increases. For example, the probability that the pixel included in the inner region of the first contour line 311 is included in the lesion region may be high. However, the probability that the pixel included between the first contour line 311 and the second contour line 312 is included in the lesion region may be relatively low. Accordingly, the medical imaging device 100 may display the first contour line 311 thicker than the second contour line 312.

The medical imaging device 100 may apply different colors to the contour lines according to the probability that pixels inside the contour line are included in the lesion region. For example, the probability that the pixel included in the inner region of the first contour line 311 is included in the lesion region may be high. However, the probability that the pixel included between the first contour line 311 and the second contour line 312 is included in the lesion region may be relatively low. Accordingly, the medical imaging device 100 may display the first contour line 311 in red and the second contour line 312 in orange.

The medical imaging device 100 may display the region between the contour lines in different colors, based on the probability that pixels inside the contour lines are included in the lesion region. For example, the probability that the pixel included in the inner region of the first contour line 311 is included in the lesion region may be high. However, the probability that the pixel included between the first contour line 311 and the second contour line 312 is included in the lesion region may be relatively low. Therefore, the medical imaging device 100 may fill the inside of the first contour line 311 in red and display the region between the second contour line 312 and the first contour line 311 in orange. The medical imaging device 100 may adjust the transparency such that the original medical image is not obstructed by the painted color.

The probability that the pixel included in one of a plurality of lines included in the contour line is included in the lesion region may be included in a specific threshold range. The specific threshold range may be a predetermined range. Referring to FIG. 3, the probability that the pixel included in the first contour line 311 is included in the lesion region may be included in the first threshold range. In addition, the probability that the pixel included in the second contour line 312 is included in the lesion region may be included in the second threshold range. The minimum value of the first threshold range may be greater than the maximum value of the second threshold range.

In addition, the medical imaging device 100 may generate a plurality of contours by enlarging the outline of the lesion region included in the lesion information. For example, the first contour line 311 may be an outline of the lesion region. The medical imaging device 100 may obtain the second contour line 312 by enlarging the first contour line 311. The thickness of the second contour line 312 may be thinner than that of the first contour line 311.

The medical imaging device 100 may perform outputting (230) at least one contour generated in the medical image. The output unit 130 may output the medical image and at least one contour.

The medical imaging device 100 may perform the following operations to generate at least one contour.

The medical imaging device 100 may perform generating a contour based on at least one of: information related to an overlapping lesion region between a plurality of lesions included in the medical image; or information related to relevance between the plurality of lesions, based on the obtained lesion information.

A plurality of lesions may be detected from the medical image. The lesion information may be obtained for each of the plurality of lesions. As already described above, the lesion information may include the lesion region information.

The medical imaging device 100 may obtain information related to an overlapping lesion region between a plurality of lesions, based on the lesion information. In addition, the medical imaging device 100 may obtain information related to relevance between a plurality of lesions.

The information related to relevance between the plurality of lesions is information indicating whether or not there is a medical relevance between the plurality of lesions. For example, the information related to relevance may include information on presence of coexistence, indicating whether or not a plurality of lesions may be expressed in the same patient at the same time. For example, if the first lesion cannot appear simultaneously with the second lesion, there is no coexistence, and if the first lesion can appear simultaneously with the second lesion, there is coexistence.

In addition, the information related to relevance may include information on presence of similarity, indicating whether or not there is a high possibility that the plurality of lesions are expressed at the same time. The plurality of lesions have distinct names, but in many cases, they are substantially similar to each other. For example, if the first lesion is medically expressed and the second lesion is also expressed, this means there is similarity. The expression of the second lesion when the first lesion is expressed may not necessarily mean that the first lesion is expressed when the second lesion is expressed. However, aspects are not limited thereto, and the expression of the second lesion when the first lesion is expressed may mean that the first lesion is expressed when the second lesion is expressed.

In addition, if the expression of the first lesion and the second lesion are independent and the expression of the first lesion has no effect on the expression of the second lesion, there is no similarity between the first lesion and the second lesion. In addition, if the expression of the second lesion has no effect on the expression of the first lesion, there is no similarity between the first lesion and the second lesion.

The medical imaging device 100 may obtain information related to relevance based on a rule base or a machine learning model. The medical imaging device 100 may obtain information related to relevance based on the database 120. The medical imaging device 100 may obtain first lesion information on the first lesion. In addition, the medical imaging device 100 may obtain second lesion information on the second lesion. The medical imaging device 100 may obtain, from the first lesion information, a first lesion identifier including at least one of a code, a name, and a type of the first lesion. In addition, the medical imaging device 100 may obtain, from the second lesion information, a second lesion identifier including at least one of a code, a name, and a type of the second lesion. The medical imaging device 100 may obtain information related to relevance between the first lesion and the second lesion from the database based on the first lesion identifier and the second lesion identifier. For example, the database may store information related to relevance according to the first identifier and the second lesion identifier in advance. The medical imaging device 100 may derive, from the database, information related to relevance corresponding to the first identifier and the second identifier.

The medical imaging device 100 may obtain information related to relevance from elsewhere than the database 120. The medical imaging device 100 may apply the first lesion information and the second lesion information to the machine learning model to obtain information related to relevance. The machine learning model may be a machine learning model of the relevance between the first lesion and the second lesion. The medical imaging device 100 may obtain information related to relevance from a medical practitioner. In addition, the medical imaging device 100 may obtain information related to relevance from the lesion information.

The first lesion information related to the first lesion may include information on lesions having a similarity to the first lesion, and information on lesions having coexistence with the first lesion. The medical imaging device 100 may determine whether or not the second lesion has similarity to or coexistence with the first lesion based on the first lesion information.

The medical imaging device 100 may obtain, from a medical practitioner, information related to relevance based on an input signal. In addition, the medical imaging device 100 may obtain information related to relevance from an external device.

The medical imaging device 100 may perform determining a size of an overlapping region between the region of the first lesion and the region of the second lesion, based on the first lesion information and the second lesion information included in the plurality of lesions, so as to generate at least one contour.

As described above, the medical imaging device 100 may obtain the first lesion information on the first lesion and the second lesion information on the second lesion. The medical imaging device 100 may obtain the region information of the first lesion in the medical image from the first lesion information, and the region information of the second lesion in the medical image from the second lesion information. In addition, the medical imaging device 100 may determine the size of the overlapping region between the first lesion region and the second lesion region. The size of the overlapping region may be expressed by at least one of: the number of pixels in the overlapping region; the area of the overlapping region; the horizontal length of the overlapping region; or the vertical length of the overlapping region.

In this example, the region of the first lesion and the region of the second lesion may simply mean the region of the first lesion and the region of the second lesion, but are not limited thereto. The region of the first lesion may refer to an inner region of the first contour corresponding to the first lesion. In addition, the region of the second lesion may refer to an inner region of the second contour corresponding to the second lesion.

The medical imaging device 100 may perform determining information related to the probability of presence of the second lesion in the medical image based on the second lesion information. As already described, the information related to the probability of presence of the second lesion in the medical image may be probability value corresponding to each pixel value included in the medical image or probability value corresponding to a specific region included in the medical image. In this case, the specific region may correspond to the generated contour.

In addition, the medical imaging device 100 may perform generating at least one contour surrounding the first lesion, if the size of the overlapping region is greater than the first threshold value and information related to the probability of presence of the second lesion in the medical image is less than the second threshold value. The first threshold value and the second threshold value may be predetermined values. The second threshold value may be information related to the probability of presence of the first lesion in the medical image, but is not limited thereto.

The contour may be equal to or greater than the first lesion region. Since the method for generating at least one contour surrounding the first lesion has already been described above, a redundant description will be omitted.

If the size of the overlapping region is greater than the first threshold value and the information related to the probability of presence of the second lesion in the medical image is less than the second threshold value, the medical imaging device 100 may only generate at least one contour surrounding the first lesion, but may not generate at least one contour surrounding the second lesion. This is because, since the size of the overlapping region is greater than the first threshold value, the first lesion and the second lesion substantially overlap with each other, and since the information related to the probability of presence of the second lesion in the medical image is less than the second threshold value, the importance of the second lesion in the medical image may be relatively low.

The medical imaging device 100 may perform determining presence of pathological similarity between the first lesion and the second lesion in order to generate at least one contour. The presence of similarity may be included in the information related to relevance. Since the information on the presence of similarity has already been described above, a redundant description will be omitted. In addition, the medical imaging device 100 may determine presence of similarity as a rule base based on a database, obtain it from a machine learning model, receive it from a medical practitioner, or obtain it from the lesion information. Since the process of obtaining the information related to relevance has already been described above, a redundant description will be omitted.

The medical imaging device 100 may perform determining presence of coexistence between the first lesion and the second lesion for a same region. Since the information on the presence of coexistence has already been described, a redundant description will be omitted. In addition, the medical imaging device 100 may determine the presence of coexistence as a rule base based on a database, obtain it from a machine learning model, receive it from a medical practitioner, or obtain it from lesion information. Since the process of obtaining the information related to relevance has already been described above, a redundant description will be omitted.

If the presence of similarity indicates that the first lesion and the second lesion are similar to each other, or if the presence of coexistence indicates that the first lesion and the second lesion cannot coexist with each other, the medical imaging device 100 may perform generating at least one contour surrounding the first lesion, without generating at least one contour surrounding the second lesion.

If the presence of similarity indicates that the first lesion and the second lesion are similar to each other, the medical imaging device 100 may generate at least one contour surrounding only the first lesion. This is because the presence of similarity means that if the first lesion is expressed, the second lesion can be expressed. If the presence of similarity indicates that the first lesion and the second lesion are not similar to each other, the medical imaging device 100 may generate both the at least one contour corresponding to the first lesion and the at least one contour corresponding to the second lesion.

In addition, if the presence of coexistence indicates that the first lesion and the second lesion cannot coexist, the medical imaging device 100 may generate at least one contour surrounding only one of the first lesion or the second lesion. In order to determine for which of the first lesion or the second lesion a contour is to be generated, the medical imaging device 100 may compare probabilities of presence the first lesion and the second lesion in the medical image. In addition, if the probability of presence the first lesion in the medical image is higher than that of the second lesion, the medical imaging device 100 may generate at least one contour surrounding the first lesion. The medical imaging device 100 may not generate at least one contour surrounding the second lesion. Conversely, if the probability of presence the first lesion in the medical image is lower than that of the second lesion, the medical imaging device 100 may generate at least one contour surrounding the second lesion. The medical imaging device 100 may not generate at least one contour surrounding the first lesion.

The medical imaging device 100 may further perform arranging the plurality of lesion information in the order of higher probability of presence in the medical image, based on the plurality of lesion information. The medical imaging device 100 may arrange information on a plurality of lesions in the order of higher probability of presence in one medical image, such that it 100 does not output the contour corresponding to the lesion with a low probability of presence if there is no coexistence between the two lesions.

In addition, if the presence of coexistence indicates that the first lesion and the second lesion may coexist, the medical imaging device 100 may generate both the at least one contour corresponding to the first lesion and the at least one contour corresponding to the second lesion.

FIG. 4 illustrates pseudo-code of a method for operating a medical imaging device.

A line 410 may represent a set of contours corresponding to a plurality of detected lesions. C may include a total of M elements. That is, $C = \{c1, c2, \ldots, cM\}$.

The medical imaging device 100 may perform the for statement while the index i increases from 1 to M−1. In a line 420, R(i) is a function that arranges the contour elements in the set C in the order of higher probability of presence in the medical image. That is, R(1) may output at least one contour of a lesion having the highest probability of presence in the medical image. In addition, R(M−1) may output at least one contour of a lesion having the lowest probability of presence in the medical image. By R(i), the medical imaging device 100 may assign cp with a contour corresponding to the lesion having the i-th highest probability. As i increases by R(i), the medical imaging device 100 may assign cp with a contour of a lesion having a low probability of presence in the medical image.

In a line 430, D(cp) is a function for outputting lesion information corresponding to the contour cp. By D(cp), the medical imaging device 100 may assign dp with the lesion information corresponding to cp.

The medical imaging device 100 may perform the for statement while the index j increases from 2 to M. In FIG. 4, the index j increases from 2, but aspects are not limited thereto. The index j may increase from i+1 to M.

In a line 440, R(j) is a function that arranges the contour elements in the set C in the order of higher probability of presence in the medical image. By R(j), the medical imaging device 100 may assign cq with a contour corresponding to the lesion having the j-th highest probability.

In line 450, D(cq) is a function for outputting lesion information corresponding to the contour cq. By D(cq), the medical imaging device 100 may assign dq with the lesion information corresponding to cq.

In a line 460, IoU(cp, cq) may indicate the size of a region where the regions of the contour cp and cq overlap with each other. In addition, S(cq) may represent probability that a pixel inside contour cq is included in the lesion region.

In the line 460, if the size of an overlapping region between the regions of the contour cp and the contour cq is greater than a threshold value MTdq, and if the probability that the pixel inside the contour cq is included in the lesion region is less than a threshold value STdq, the medical imaging device 100 may perform a line 470.

In the line 470, Sim(dp, dq) may output information on the presence of similarity between the lesion information dp and the lesion information dq. If Sim(dp, dq) is 1, it may indicate that there is a similarity between the lesion information dp and the lesion information dq. In addition, if Sim(dp, dq) is 0, it may indicate that there is no similarity between the lesion information dp and the lesion information dq.

CoOcc(dp, dq) may output information on the presence of coexistence between the lesion information dp and the lesion information dq. If CoOcc(dp, dq) is 1, it may indicate that there is coexistence between the lesion information dp and the lesion information dq. In addition, if CoOcc(dp, dq) is 0, it may indicate that there is no coexistence between the lesion information dp and the lesion information dq.

In the line 470, if there is a similarity between the lesion information dp and the lesion information dq and if there is no coexistence between the lesion information dp and the lesion information dq, the medical imaging device 100 may perform a line 480.

If the above condition is satisfied, the medical imaging device 100 may remove the contour cq from the set C. That is, if the size of the region where the region of the contour cp and the region of the contour cq overlap with each other is greater than a threshold value Mtdq, and if the probability that the pixel inside the contour cq is included in the lesion region is less than a threshold value (STdq), and if there is a similarity between the lesion information dp and the lesion information dq, and if there is no coexistence between the lesion information dp and the lesion information dq, the medical imaging device 100 may remove the contour cq from the set C. In a line 490, the medical imaging device 100 may output the contour included in the set C to the output unit 130. That is, the medical imaging device 100 may not output the contour cq.

FIGS. 5 to 8 are diagrams illustrating medical images displayed by the medical imaging device.

The medical imaging device 100 may display an arrow or text near the contour. The text may include content related to the contour. FIGS. 5 to 8 are examples of placement of arrows or text positioned near the contour. Referring to FIGS. 5 to 8, the medical imaging device 100 may arrange arrows and text such that the user can clearly understand the meaning of the contour.

Figure 5:
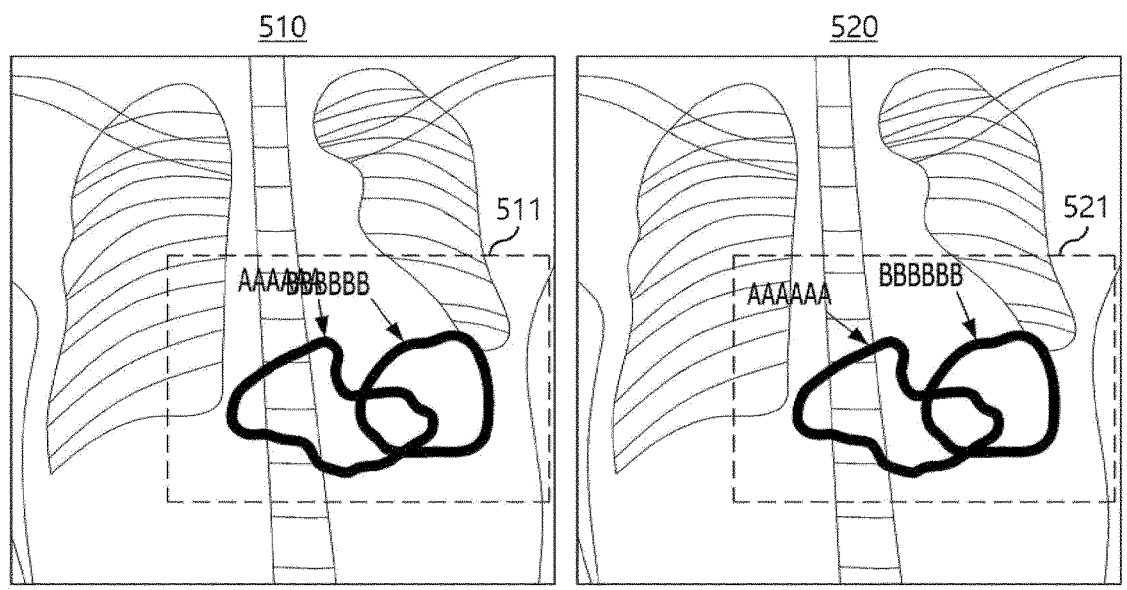
FIG. 5 illustrates a medical image displayed by a medical imaging device.

Referring to FIG. 5, the medical imaging device 100 may output a contour together with a medical image. In addition, the medical imaging device 100 may display arrows and text near the contour. The arrows may connect between the contour and text. In addition, the text may describe the lesion included in the contour. The medical imaging device 100 may obtain text based on the lesion information.

A medical image 510 represents an example in which the arrows and text are incorrectly displayed. Referring to a box 511, a plurality of texts are displayed as being overlapped with each other. In addition, referring to the box 511, at least some of the plurality of arrows may cross each other. Therefore, a medical practitioner may not be able to recognize the contents of the text.

A medical image 520 represents a medical image normally displayed by the medical imaging device 100. Referring to a box 521, arrows included in the medical image 520 do not cross each other. In addition, texts are not overlapped with each other. Therefore, the medical practitioner can clearly understand the meaning of the contour.

Figure 6:
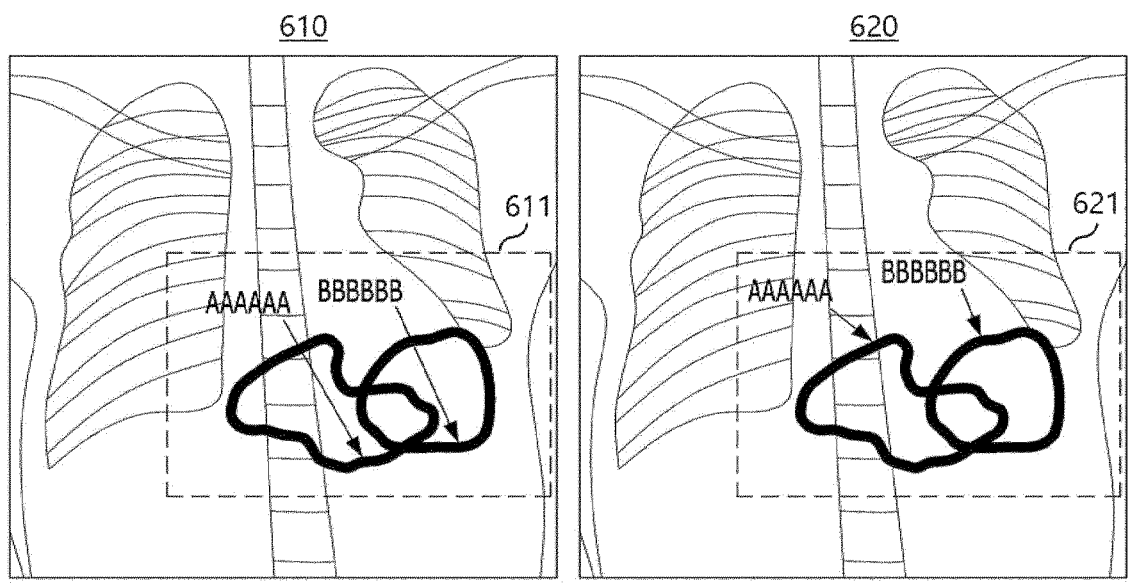
FIG. 6 illustrates a medical image displayed by a medical imaging device.

Referring to FIG. 6, a medical image 610 represents an example in which arrows and text are incorrectly displayed. Referring to a box 611, the arrows are crossing the contour. If the arrow crosses the contour, then the length of the arrow may be long, and the distance between the contour pointed to by the arrow and the text may be far from each other. Therefore, it may be difficult for the medical practitioner to determine which contour the text is intended for.

A medical image 620 represents a medical image normally displayed by the medical imaging device 100. Referring to a box 621, arrows included in the medical image 620 does not cross the contour. Therefore, the medical practitioner can clearly understand the meaning of the contour.

Figure 7:
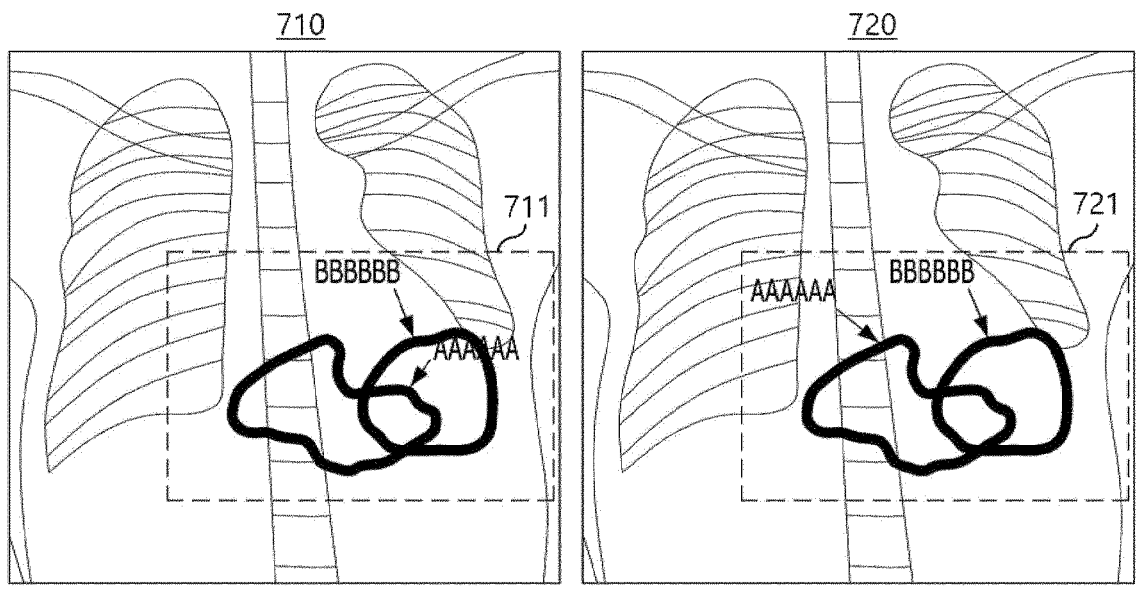
FIG. 7 illustrates a medical image displayed by a medical imaging device.

Referring to FIG. 7, a medical image 710 represents an example in which arrows and text are incorrectly displayed. Referring to a box 711, arrows and text are displayed over the contour. If arrows and text are displayed over the contour, the readability of the text may be reduced. Therefore, a medical practitioner may not be able to recognize the contents of the text.

A medical image 720 represents a medical image normally displayed by the medical imaging device 100. Referring to a box 721, arrows and text included in the medical image 720 are not displayed over the contour. Therefore, the medical practitioner can clearly understand the meaning of the contour.

Figure 8:
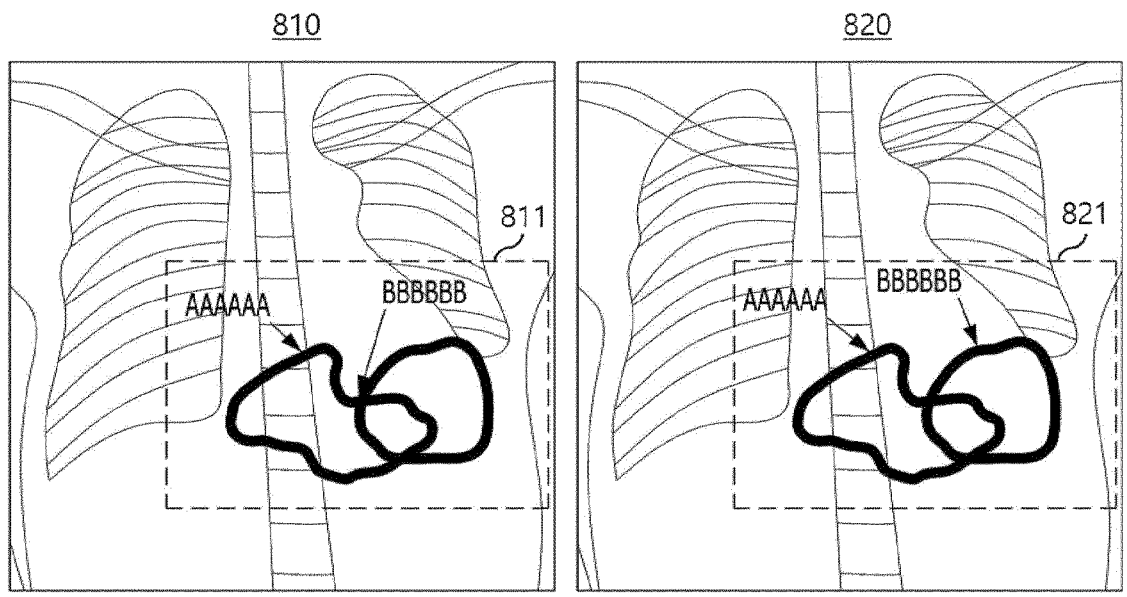
FIG. 8 illustrates a medical image displayed by a medical imaging device.

Referring to FIG. 8, a medical image 810 represents an example in which arrows and text are incorrectly displayed. Referring to a box 811, an arrow is displayed above an intersection point of the two contours. If an arrow is displayed at the intersection point of two contours, it may be difficult to understand which contour the arrow points to. Therefore, the medical practitioner may not be able to recognize the text corresponding to the contour.

A medical image 820 represents a medical image normally displayed by the medical imaging device 100. Referring to a box 821, the arrow included in the medical image 820 is not displayed at the intersection point of the two contours. Accordingly, the medical practitioner can clearly understand the text corresponding to the contour.

Figure 9:
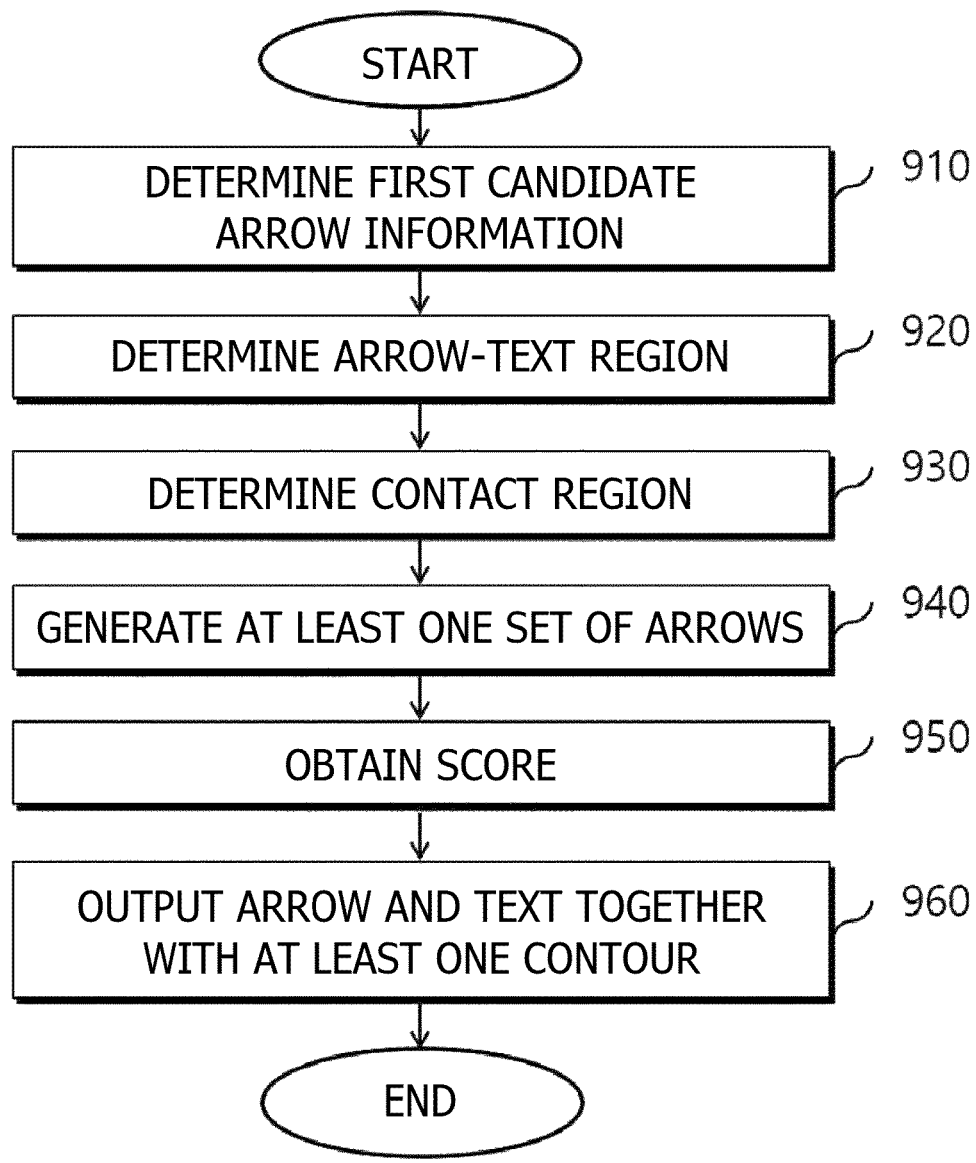
FIG. 9 is a flowchart illustrating an operation of a medical imaging device.

FIG. 9 is a flowchart illustrating an operation of a medical imaging device. In addition, FIGS. 10 to 13 are diagrams for explaining an operation of the medical imaging device.

In order to output at least one contour, the medical imaging device 100 may perform determining (910) first candidate arrow information for a plurality of first candidate arrows pointing to a first one of the at least one contour.

The candidate arrow information may include at least one of: position information on a start point of the arrow; position information on an end point of the arrow; information on a direction of the arrow; and information on a length of the arrow.

Figure 10:
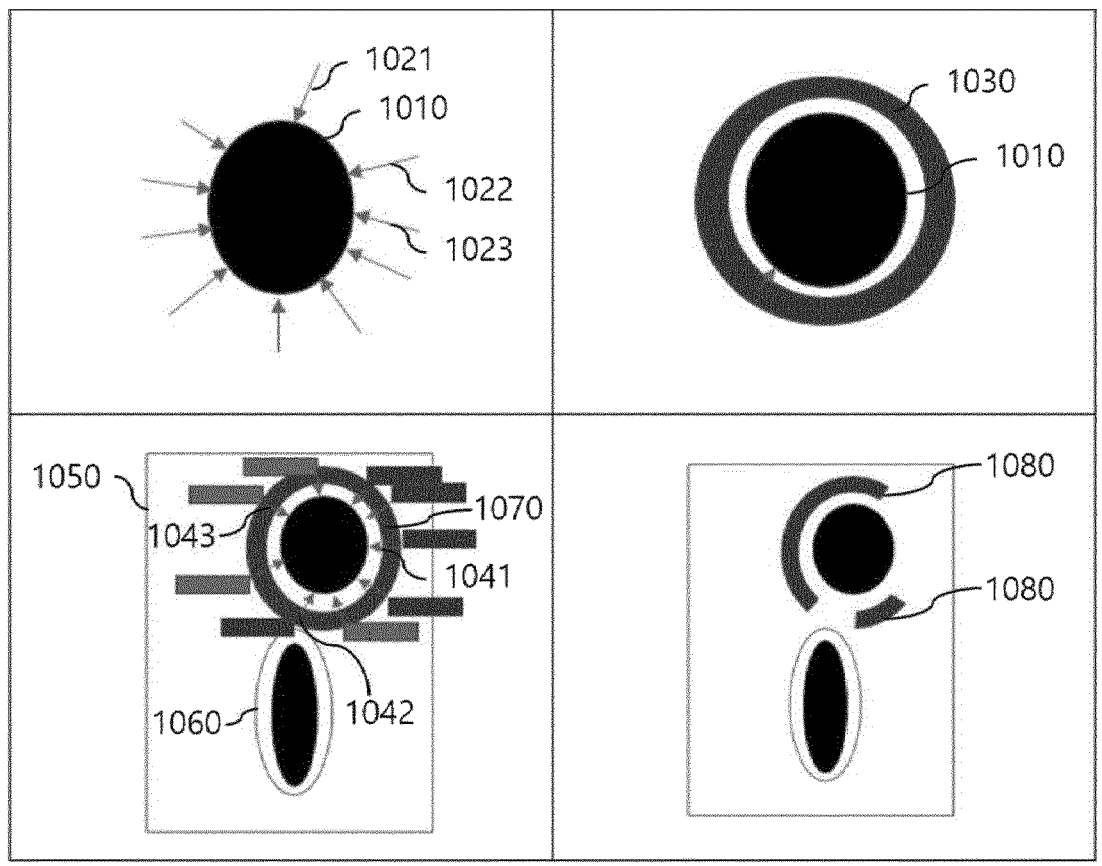
FIG. 10 is a diagram for explaining an operation of a medical imaging device.

Referring to an image on the upper left side of FIG. 10, the medical imaging device 100 may obtain a plurality of first candidate arrows 1021, 1022, and 1023 indicating a first contour 1010 of the at least one contour. The plurality of first candidate arrows 1021, 1022, and 1023 may be substantially perpendicular to the first contour 1010. The plurality of first candidate arrows 1021, 1022, and 1023 may include a start point and an end point. In the present disclosure, the start point of the arrow may represent a point on the arrow that is closest to the contour. In the present disclosure, the end point may represent a point on the arrow opposite the start point. The start point of the arrow may be the head of the arrow, but is not limited thereto, and the end point of the arrow may be the head of the arrow.

The positions of the start points of the plurality of first candidate arrows 1021, 1022, and 1023 may be randomly determined on the contour 1010. In addition, the number of the plurality of first candidate arrows 1021, 1022, and 1023 may be predetermined. Although reference numerals are not assigned to all of the plurality of first candidate arrows in FIG. 10, the number of the plurality of first candidate arrows 1021, 1022, and 1023 may be ten. The lengths of the plurality of first candidate arrows 1021, 1022, and 1023 may be predetermined. In addition, the lengths of the plurality of first candidate arrows 1021, 1022, and 1023 may be randomly determined within a predetermined range.

Figure 11:
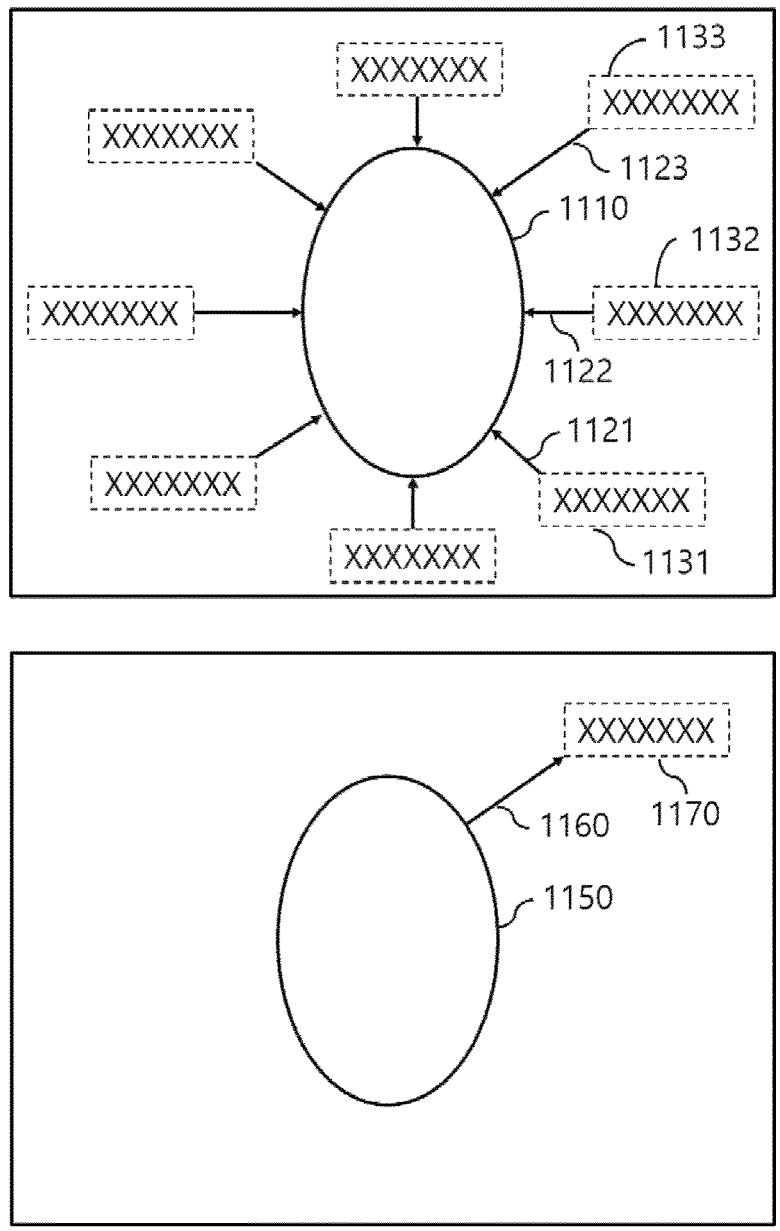
FIG. 11 is a diagram for explaining an operation of a medical imaging device.

Referring to FIG. 11, the medical imaging device 100 may obtain a plurality of first candidate arrows 1121, 1122, and 1123 pointing to the first contour 1110 of the at least one contour. Text boxes 1131, 1132, and 1133 may be positioned at the end points of the plurality of first candidate arrows 1121, 1122, and 1123. Text may be displayed in the text boxes 1131, 1132, and 1133. The plurality of first candidate arrows 1121, 1122, and 1123 may correspond one-to-one with the text boxes 1131, 1132, and 1133.

Positions between the plurality of first candidate arrows 1121, 1122, and 1123 and the text boxes 1131, 1132, and 1133 may be determined in a predetermined manner. The positions of the text boxes 1131, 1132, and 1133 may be set based on the directions of the plurality of first candidate arrows 1121, 1122, and 1123. In addition, the medical imaging device 100 may set the position of the text box such that one of the plurality of first candidate arrows 1121, 1122, and 1123 is positioned at a corner or side of the text box. For example, if the start point of a first candidate arrow 1121 is in the upper left direction of the end point, the upper left vertex of the text box 1131 may be close to the end point of the first candidate arrow 1121. In addition, if the start point of the first candidate arrow 1122 is in the left direction of the end point, the left side of the text box 1132 may be close to the end point of the first candidate arrow 1122. Since FIG. 11 illustrates the relationship between the arrow and the text, further description will be omitted.

The positional relationship between the candidate arrows and the text boxes illustrated in FIG. 11 is an example, and there may be various other positional relationships between the candidate arrow and the text box.

The head of a candidate arrow 1160 may be positioned at the end point. That is, the start point of the candidate arrow 1160 may be close to or in contact with a contour 1150, and the end point of the candidate arrow 1160 may be close to or in contact with the corner or side of the text region 1170 (e.g., a box-shaped text region, and the like).

Referring to FIG. 9 again, the medical imaging device 100 may perform determining (920) an arrow-text region 1030 on the outside of the first contour 1010.

Referring to the image on the upper right side of FIG. 10, the arrow-text region 1030 may be a region including an end point of an arrow and a portion of a text box. In the arrow-text region 1030, the end point of the arrow and the text box may be adjacent to each other.

Figure 12:
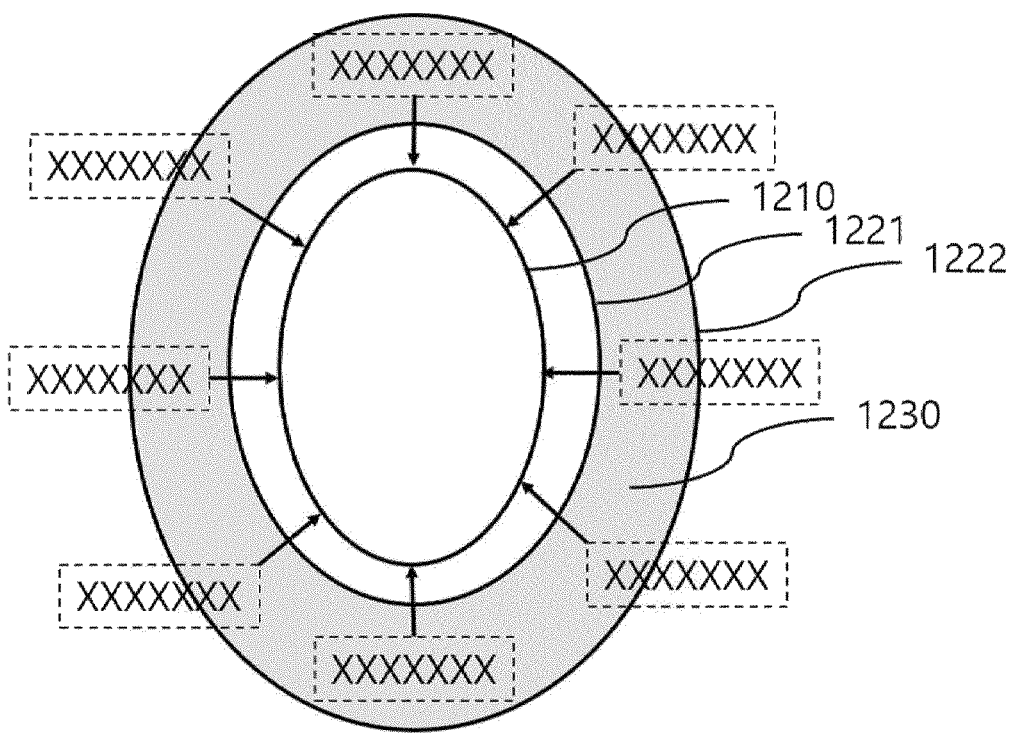
FIG. 12 is a diagram for explaining an operation of a medical imaging device.

Referring to FIG. 12, the medical imaging device 100 may generate a contour 1210. The medical imaging device 100 may enlarge the contour 1210 to generate a first enlarged contour 1221. In addition, the medical imaging device 100 may enlarge the contour 1210 to generate a second enlarged contour 1222. The second enlarged contour 1222 may include the first enlarged contour 1221. The medical imaging device 100 may use the contour 1210 and a predetermined multiple to obtain the first enlarged contour 1221 and the second enlarged contour 1222. The medical imaging device 100 may determine a region between the first enlarged contour 1221 and the second enlarged contour 1222 as an arrow-text region 1230. The arrow-text region 1230 may have a ring shape surrounding the first contour 1210 without contacting the first contour 1210.

If the end points of the plurality of first candidate arrows generated at 910 are not included in the arrow-text region 1030, the medical imaging device 100 may adjust start points or end points of the plurality of first candidate arrows such that the end points of the plurality of first candidate arrows are included in the arrow-text region 1030.

Referring to FIG. 9 again, the medical imaging device 100 may perform determining (930), in the arrow-text region, a contact region where one side of the text box corresponding to the plurality of first candidate arrows and displaying lesion information for the first contour meets one end of a plurality of first candidate arrows included in the first candidate arrow information. In this case, the one side may indicate a corner or a side of the text box. In addition, the one end may be a start point or an end point of the candidate arrow.

Referring to the image on the lower left side of FIG. 10, the medical imaging device 100 may determine a text to be included in the text box based on lesion information. In addition, the medical imaging device 100 may determine the size of the text box based on the font and content of the text. The medical imaging device 100 may arrange text boxes at end points of a plurality of first candidate arrows 1041, 1042, and 1043.

The content of the text may include at least one of: information on the type of the lesion; information on the probability of presence of the lesion in the medical image; information on a shape of the lesion; the size of the lesion; and the probability of presence of the lesion in a unit region of the medical image.

The medical imaging device 100 may determine information on the text box. The information on the text box may include a size of the text box, a height of the text box, a width of the text box, or position information of the text box, and the like.

The position of the text box may be determined based on the information on the arrow of the medical imaging device 100. For example, the medical imaging device 100 may position one corner or side of the text box within a predetermined distance from the end point of the arrow.

The medical imaging device 100 may determine whether or not text boxes corresponding to the plurality of first candidate arrows 1041, 1042, and 1043 can be positioned in the medical image. In addition, the medical imaging device 100 may determine, as a contact region, a region allowing a text box to be positioned in the medical image among an arrow-text region 1070. For example, a partial region of the text box corresponding to the first candidate arrow 1041 may be positioned outside a medical image 1050. The medical imaging device 100 may determine the contact region by removing, from the arrow-text region 1070, a region where the first candidate arrow 1041 is present.

In addition, the medical imaging device 100 may determine whether or not text boxes corresponding to the plurality of first candidate arrows 1041, 1042, and 1043 overlap with an object. In addition, the medical imaging device 100 may determine a region in which the text box does not overlap with the object as the contact region. In this case, the object may include at least one of a contour, another text box, or another arrow. For example, a partial region of the text box corresponding to the first candidate arrow 1042 may overlap with another contour 1060. The medical imaging device 100 may determine the contact region by removing, from the arrow-text region 1070, a region where the first candidate arrow 1042 is present.

If the text box corresponding to the first candidate arrow 1043 is positioned in the medical image and does not overlap with an object, the medical imaging device 100 may obtain the contact region by using the region including the end point of a first candidate arrow 1040.

Referring to the image on the lower right side of FIG. 10, through the process described above, the medical imaging device 100 may obtain a portion of the arrow-text region 1070 as a contact region 1080. The medical imaging device 100 may select a plurality of candidate arrows of which end points are included in the contact region. In addition, at least one set of arrows may be generated by using the selected candidate arrows.

Referring to FIG. 9 again, the medical imaging device 100 may perform generating (940), based on the determined contact region, the at least one set of arrows for displayable positions of the text box for the first contour and the arrows.

Figure 13:
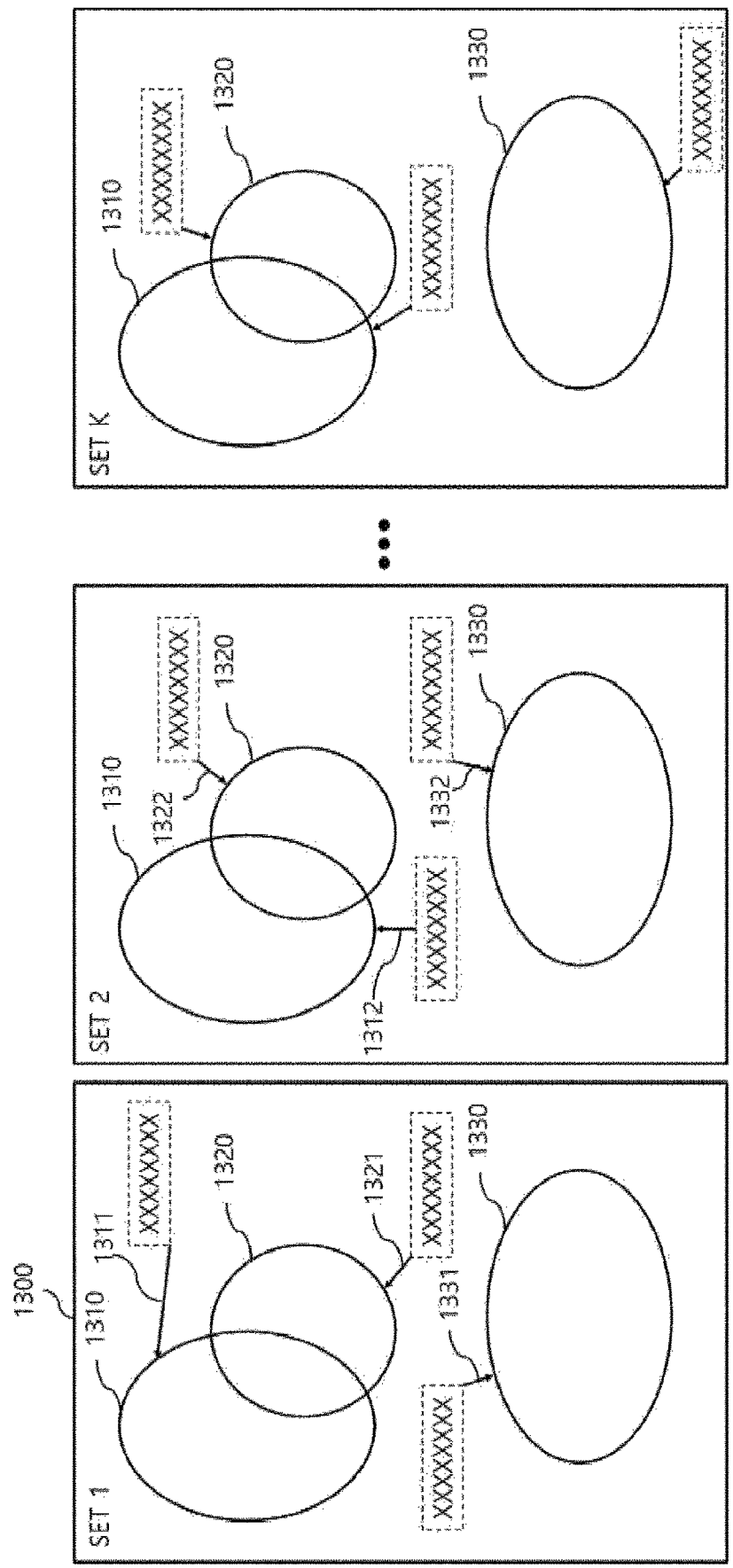
FIG. 13 is a diagram for explaining an operation of a medical imaging device.

Referring to FIG. 13, a plurality of contours 1310, 1320, and 1330 may be included in the medical image. The medical imaging device 100 may determine a contact region for each of the plurality of contours 1310, 1320, and 1330, based on 910 to 930. In addition, the medical imaging device 100 may determine a plurality of candidate arrows for each of the plurality of contours 1310, 1320, and 1330. The medical imaging device 100 may select a plurality of candidate arrows of which end points are included in the contact region. In addition, the medical imaging device 100 may remove a candidate arrow of which an end point is not included in the contact region.

The medical imaging device 100 may generate a set of arrows by selecting one candidate arrow per contour, from among a plurality of candidate arrows of which at least a portion is included in the contact region. That is, the medical imaging device 100 may select one of a plurality of candidate arrows that corresponds to one contour and generate a set of arrows.

For example, referring to SET 1 of FIG. 13, the medical imaging device 100 may select an arrow 1-1 1311 from among a plurality of candidate arrows for the first contour 1310. In addition, referring to SET 1, the medical imaging device 100 may select an arrow 2-1 1321 from among a plurality of candidate arrows for the second contour 1320. In addition, referring to SET 1, the medical imaging device 100 may select an arrow 3-1 1331 from among a plurality of candidate arrows for a third contour 1330. The arrow 1-1 1311, the arrow 2-1 1321, and the arrow 3-1 1331 may be included in SET 1.

Referring to SET 2 of FIG. 13, the medical imaging device 100 may select an arrow 1-2 1312 from among a plurality of candidate arrows for the first contour 1310. In addition, referring to SET 2, the medical imaging device 100 may select an arrow 2-2 1322 from among a plurality of candidate arrows for the second contour 1320. In addition, referring to SET 2, the medical imaging device 100 may select an arrow 3-2 1332 from among a plurality of candidate arrows for the third contour 1330. The arrow 1-2 1312, the arrow 2-2 1322, and the arrow 3-2 1332 may be included in SET 2.

The medical imaging device 100 may generate a predetermined number of sets. The medical imaging device 100 may randomly select an arrow to be included in the set from among a plurality of candidate arrows. The medical imaging device 100 may position the text box at the end point of the arrow according to a predetermined method. The medical imaging device 100 may include arrow information in the set of arrows. That is, the medical imaging device 100 may include and store the arrow information corresponding to each of the plurality of contours in the set of arrows.

The at least one set of arrows may include at least one of arrow information or information on text box. As already described, the information on the text box may include a size of the text box, a height of the text box, a width of the text box, or position information of the text box, and the like.

Referring to FIG. 9 again, the medical imaging device 100 may perform obtaining (950) a score for each of the at least one set of arrows. The score indicates a degree of convenience for a medical practitioner to examine at least one of the medical images, the contours, the arrows, and the text. A higher score indicates that the medical practitioner can conveniently review at least one of the medical images, the contours, the arrows, and the text. Obtaining the score will be described in more detail with reference to FIGS. 17 and 18.

The medical imaging device 100 may perform selecting (960) one of the at least one set of arrows based on the obtained score. The medical imaging device 100 may select the set of arrows with the highest score. For example, in FIG. 13, if SET 1 has the highest score among SET 1 and SET 2, the medical imaging device 100 may select SET 1. In addition, if the set of arrows has the highest score, but if arrows in the set of arrows cross each other, the medical imaging device 100 may not select the corresponding set of arrows.

If the first arrow corresponding to the first contour of the set of arrows and the second arrow corresponding to the second contour of the set of arrows cross each other, the medical imaging device 100 may not select the corresponding set of arrows. Alternatively, if the first arrow corresponding to the first contour of the set of arrows and the second arrow corresponding to the second contour of the set of arrows cross each other, the medical imaging device 100 may remove the arrow from the at least one set of arrows.

Referring to FIG. 9 again, the medical imaging device 100 may perform outputting (950) an arrow and text in a text box together with at least one contour, based on the selected one set of arrows. The medical imaging device 100 may output an arrow based on information on a plurality of arrows included in the selected set of arrows. In addition, the medical imaging device 100 may determine the content of the text based on the lesion information. In addition, the medical imaging device 100 may arrange the text box adjacent to the arrow based on a predetermined method. In addition, the medical imaging device 100 may display text in the text box. The text box may not be displayed.

For example, if the medical imaging device 100 selects SET 1 in FIG. 13, the medical imaging device 100 may output a medical image 1300, the plurality of contours 1310, 1320, and 1330, the plurality of arrows 1311, 1321, and 1331, and the text as in SET 1.

Figure 14:
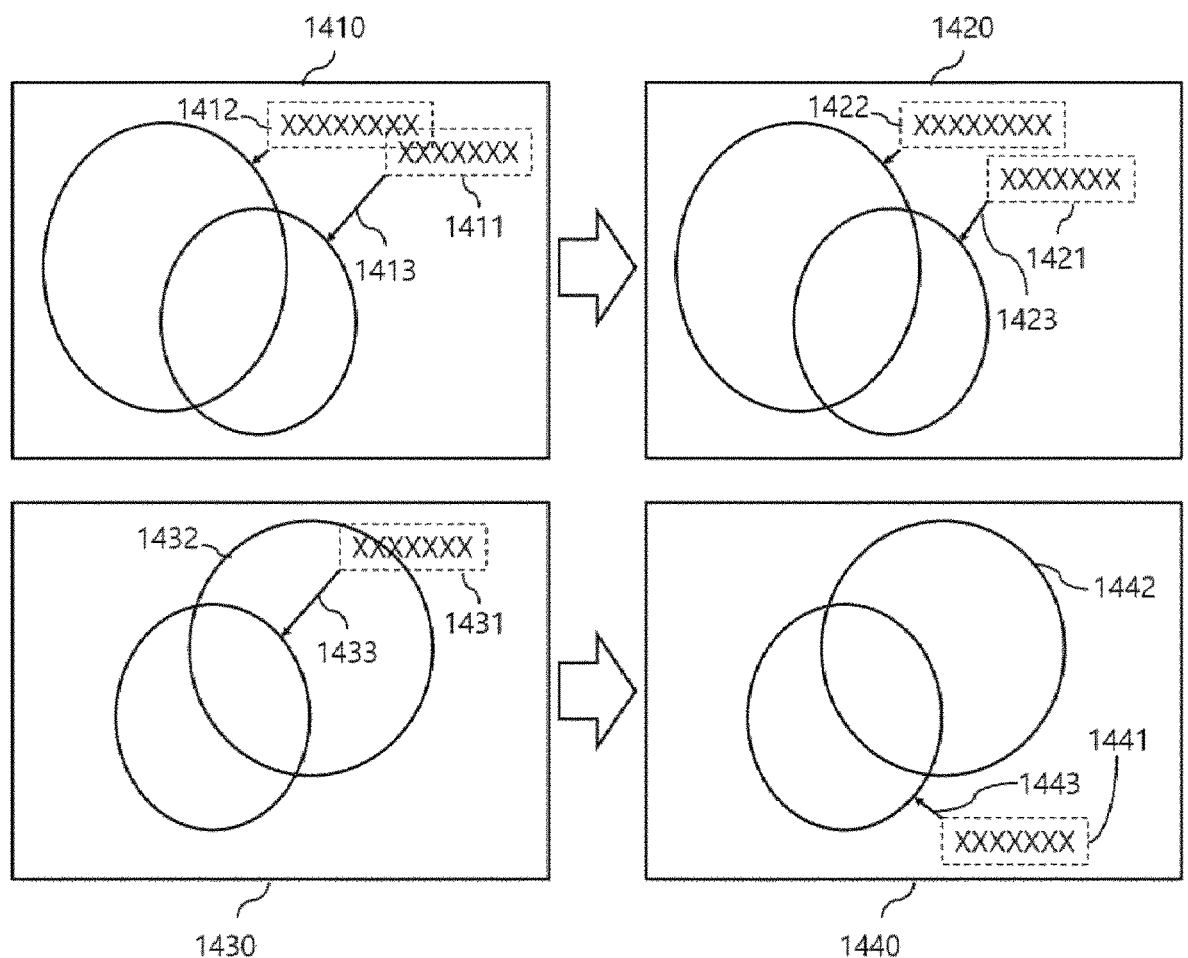
FIG. 14 is a diagram for explaining an operation of a medical imaging device.

FIG. 14 is a diagram for explaining an operation of the medical imaging device.

The medical imaging device 100 may perform the following process to determine the first candidate arrow information. The operations described below may be performed in conjunction with one of the operations 910 to 940 of FIG. 9.

If the first text box for the first contour overlaps with the second text box for the second contour or the second contour, the medical imaging device 100 may perform moving the start point or end point of the candidate arrow included in the first candidate arrow information such that the first text box does not overlap with the second text box or the second contour, so as to obtain modified first candidate arrow information.

Referring to a medical image 1410, the medical imaging device 100 may determine that a first text box 1411 for the first contour overlaps with a second text box 1412 for the second contour. The medical imaging device 100 may move a start point or an end point of a candidate arrow 1413 included in the first candidate arrow information such that the first text box 1411 does not overlap with the second text box 1412, so as to obtain the modified first candidate arrow information. For example, the medical imaging device 100 may move the candidate arrow 1413 as much as the first text box 1411 and the second text box 1412 overlap with each other.

A medical image 1420 represents a candidate arrow 1423 based on the modified first candidate arrow information. The medical imaging device 100 may obtain a modified first text box 1421 based on the candidate arrow 1423. The modified first text box 1421 may not overlap with a second text box 1422.

Referring to a medical image 1430, the medical imaging device 100 may determine that a first text box 1431 for the first contour overlaps with a second contour 1432. The medical imaging device 100 may move a start point or an end point of a candidate arrow 1433 included in the first candidate arrow information such that the first text box 1431 does not overlap with the second contour 1432, so as to obtain the modified first candidate arrow information.

A medical image 1440 represents a candidate arrow 1443 based on the modified first candidate arrow information. The medical imaging device 100 may obtain a modified first text box 1441 based on the candidate arrow 1443. The modified first text box 1441 may not overlap with a second contour 1442.

The medical imaging device 100 may perform generating at least one set of arrows based on the modified first candidate arrow information. This operation may be performed in conjunction with operation 940 of FIG. 9.

Figure 15:
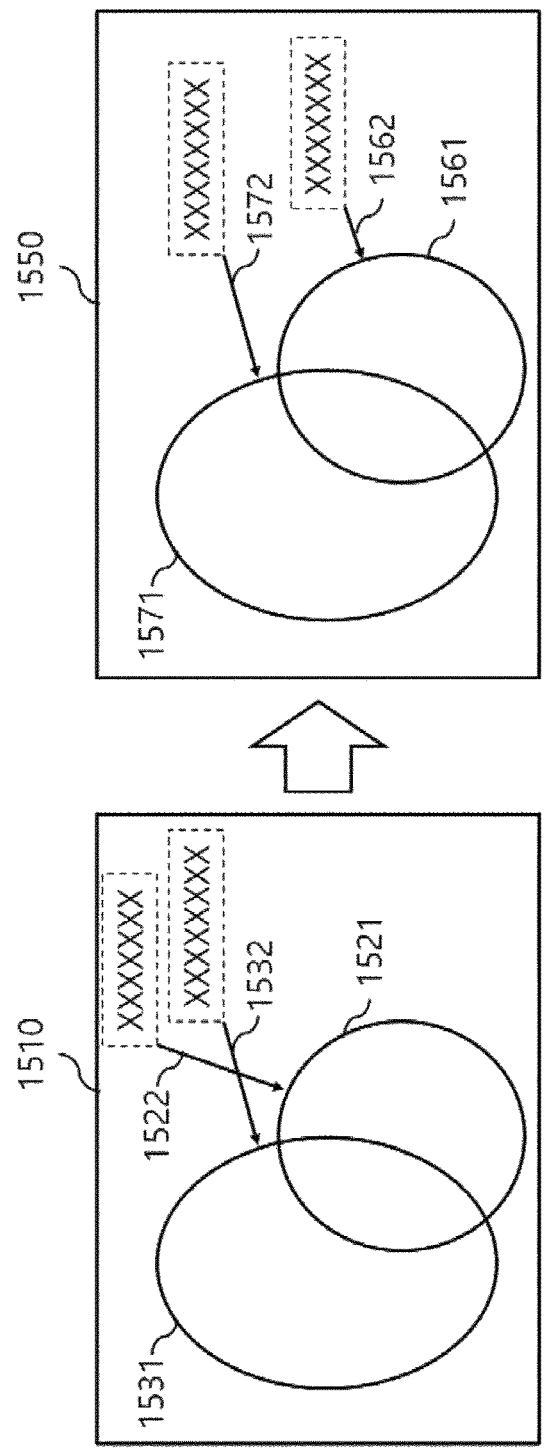
FIG. 15 is a diagram for explaining an operation of a medical imaging device.

FIG. 15 is a diagram for explaining an operation of the medical imaging device.

The medical imaging device 100 may perform the following process to determine the first candidate arrow information. The operations described below may be performed in conjunction with one of the operations 910 to 940 of FIG. 9.

The medical imaging device 100 may perform determining first candidate arrow information for a plurality of first candidate arrows pointing to a first contour 1521 of at least one contour. The plurality of first candidate arrows may include a first candidate arrow 1522. In addition, the medical imaging device 100 may perform determining second candidate arrow information for a plurality of second candidate arrows pointing to a second contour 1531 of at least one contour. The plurality of second candidate arrows may include a second candidate arrow 1532.

The medical imaging device 100 may determine whether or not the first candidate arrow 1522 of a plurality of first candidate arrows cross with the second candidate arrow 1532 of a plurality of second candidate arrows. In addition, if the first candidate arrow 1522 and the second candidate arrow 1532 cross as in a medical image 1510, the medical imaging device 100 may move the start point or the end point of the first candidate arrow 1522 such that the first candidate arrow 1522 of the plurality of first candidate arrows and the second candidate arrow 1532 of the plurality of second candidate arrows do not cross each other, so as to obtain modified first candidate arrow information.

As in a medical image 1550, the medical imaging device 100 may move the start and end points of the first candidate arrow 1522 corresponding to a first contour 1561 to obtain a modified first candidate arrow 1562. The medical imaging device 100 may obtain modified first candidate arrow information based on the modified first candidate arrow 1562.

The medical imaging device 100 may perform generating at least one set of arrows based on the modified first candidate arrow information. This operation may be performed in conjunction with operation 940 of FIG. 9.

Figure 16:
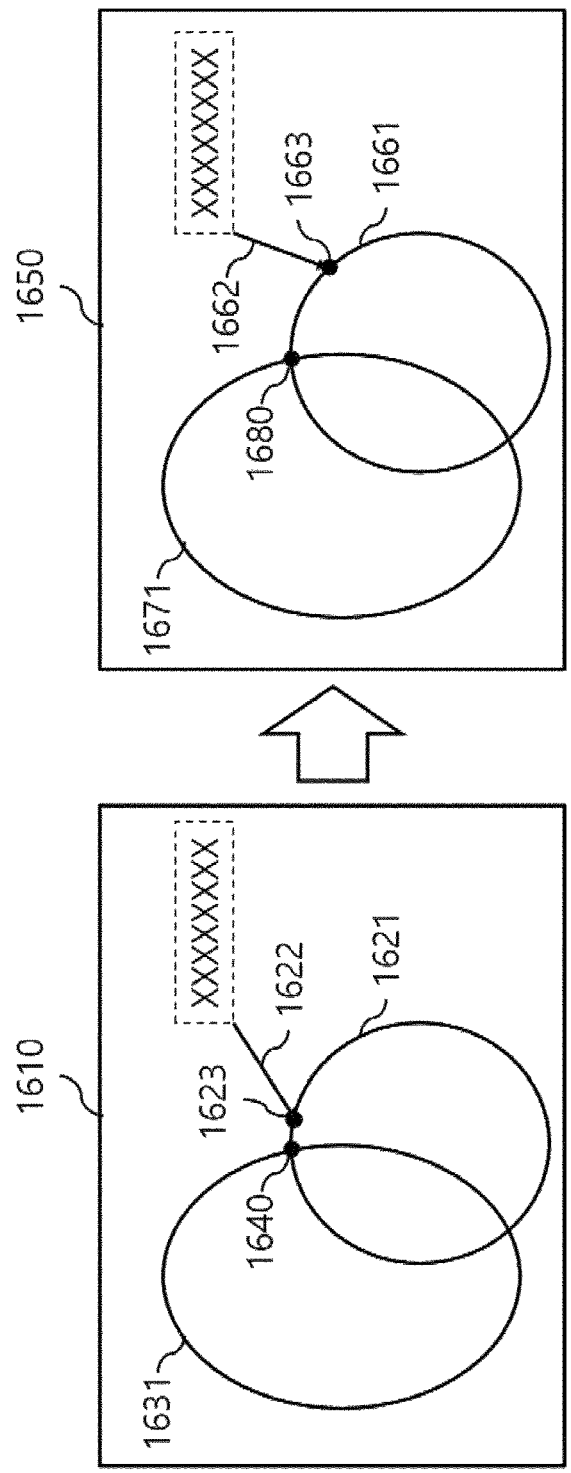
FIG. 16 is a diagram for explaining an operation of a medical imaging device.

FIG. 16 is a diagram for explaining an operation of the medical imaging device.

The medical imaging device 100 may perform the following process to determine the first candidate arrow information. The operations described below may be performed in conjunction with one of the operations 910 to 940 of FIG. 9.

Referring to a medical image 1610, the medical imaging device 100 may perform obtaining an intersection point 1640 of the first contour 1621 and a second contour 1631 of the at least one contour. The medical imaging device 100 may perform obtaining a first contact point 1623 where a first candidate arrow 1622 that is one of a plurality of first candidate arrows and the first contour 1621 meet each other.

The medical imaging device 100 may determine whether or not the first contact point 1623 is at a distance away from the intersection point 1640 by a threshold value or more. In this case, the threshold value may be a predetermined value. If the distance between the first contact point 1623 and the intersection point 1640 is less than the threshold value, the medical imaging device 100 may modify the position of the start point or the end point of the first candidate arrow 1622, which is one of the plurality of first candidate arrows, so that the first contact point 1623 is at a distance away from the intersection point 1640 by the threshold value or more. The medical imaging device 100 may perform modifying the position of the start point or the end point of the first candidate arrow 1622 to obtain the modified first candidate arrow information. The medical imaging device 100 may make the first contact point 1623 move away from the intersection point 1640 by the threshold value or more while moving the start point of the first candidate arrow 1622 along the first contour. In addition, the medical imaging device 100 may move the end point of the first candidate arrow 1622 such that the arrow is perpendicular to the contour.

A medical image 1650 represents a modified first candidate arrow 1662. The second contact point may be a contact point of the modified first candidate arrow 1662 and a first contour 1661. In addition, an intersection point 1680 may be a point where the first contour 1661 and a second contour 1671 cross each other. A second contact point 1663 may be at a distance away from the intersection point 1680 by a threshold value or more.

The medical imaging device 100 may perform generating at least one set of arrows based on the modified first candidate arrow information. This operation may be performed in conjunction with operation 940 of FIG. 9.

Figure 17:
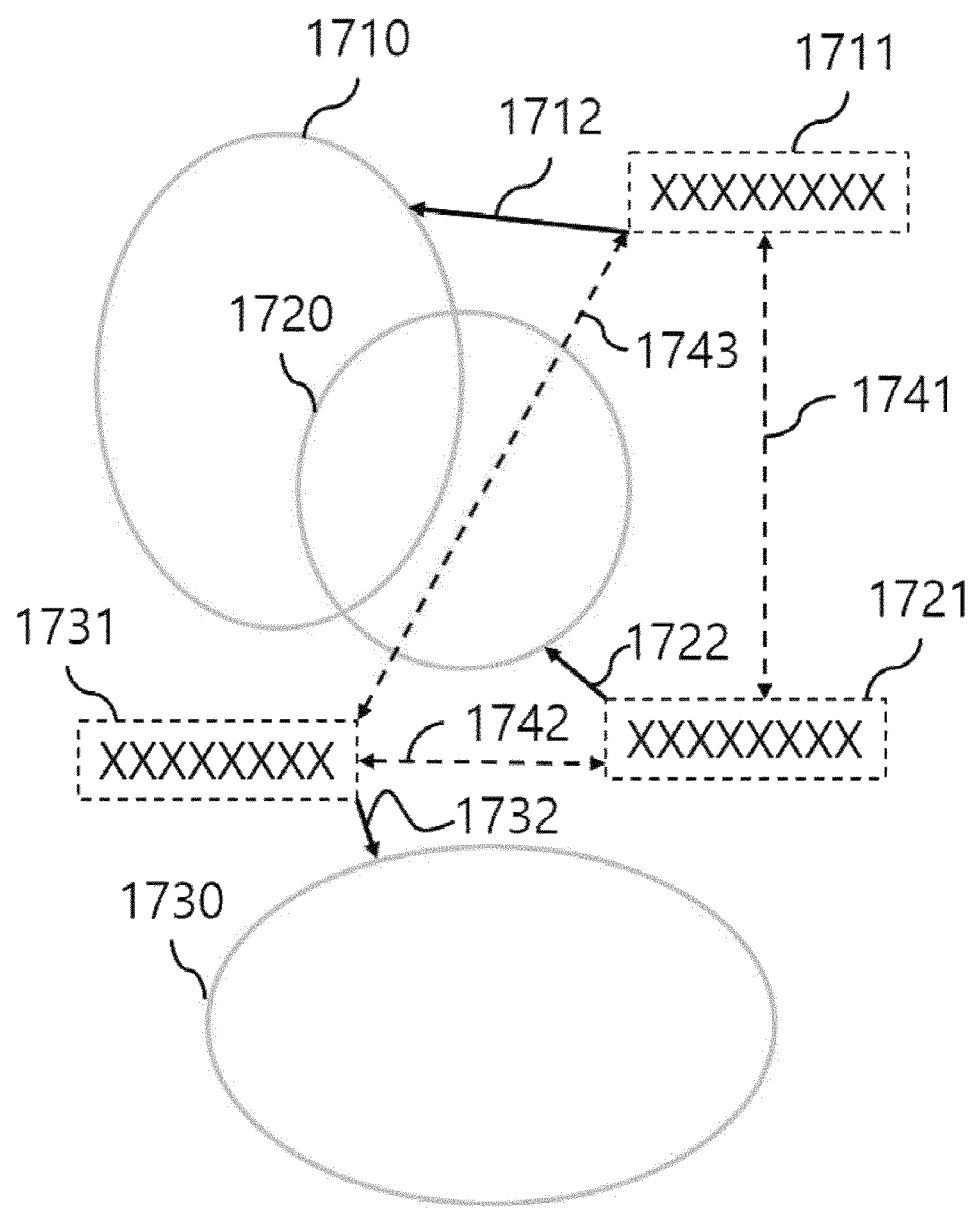
FIG. 17 is a diagram for explaining a method for obtaining a score.
Figure 18:
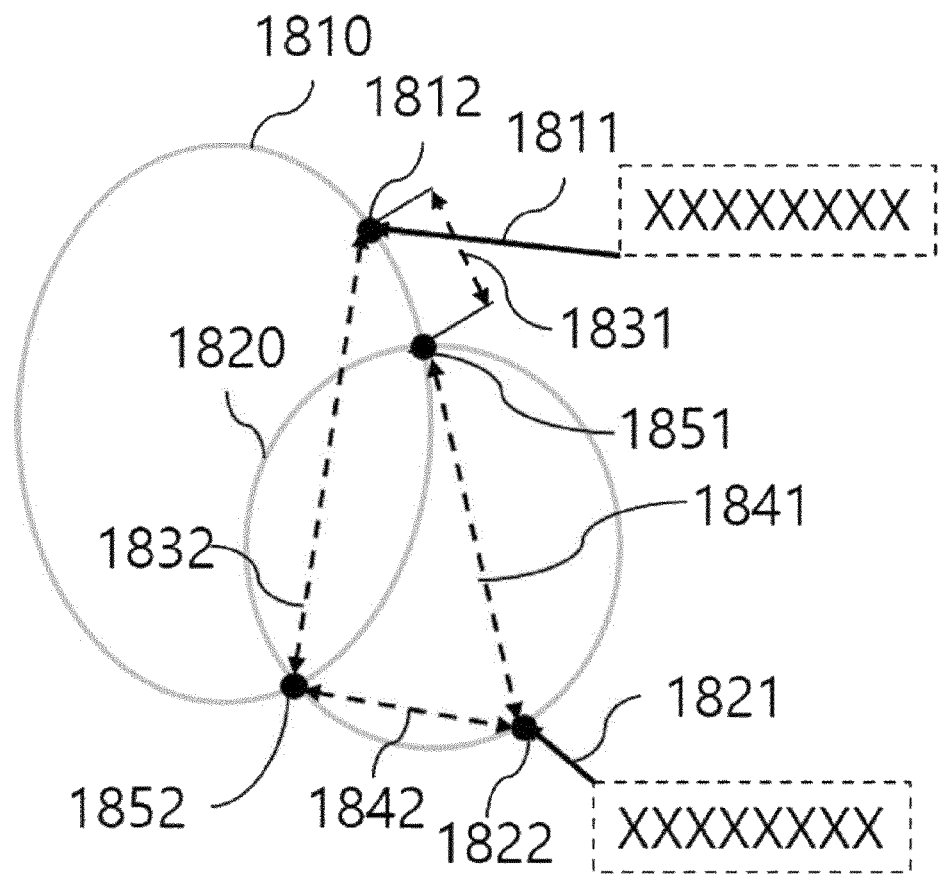
FIG. 18 is a diagram for explaining a method for obtaining a score.

FIGS. 17 and 18 are diagrams for explaining a method for obtaining a score.

As described with reference to FIG. 9, the medical imaging device 100 may perform obtaining (950) a score. The medical imaging device 100 may calculate the score according to a predetermined method. The medical imaging device 100 may calculate a score based on a distance between text boxes.

Referring to FIG. 17, the medical imaging device 100 may determine a higher score as the distance between at least one text boxes 1711, 1721, and 1731 corresponding to at least one contours 1710, 1720, and 1730 increases.

For example, the medical imaging device 100 may determine the closest distance between the text boxes. The medical imaging device 100 may determine a first distance 1741 between a first text box 1711 and a second text box 1721. The medical imaging device 100 may determine a second distance 1742 between the second text box 1721 and a third text box 1731. The medical imaging device 100 may determine a third distance 1743 between the first text box 1711 and the third text box 1731. The medical imaging device 100 may determine a score based on the first distance 1741, the second distance 1742, and the third distance 1743. The medical imaging device 100 may determine a higher score as the sum of the first distance 1741, the second distance 1742, and the third distance 1743 increases.

In addition, the medical imaging device 100 may determine a higher score as the length of the at least one arrow 1712, 1722, and 1732 corresponding to the at least one contour 1710, 1720, and 1730 decreases. The medical imaging device 100 may determine the length of the at least one arrow based on at least one candidate arrow information respectively corresponding to the at least one contour. As already described, the candidate arrow information may include the position of the start point, the position of the end point, or the length of the arrow. The medical imaging device 100 may obtain the length of the arrow from the candidate arrow information.

More specifically, the medical imaging device 100 may obtain the length of a first arrow 1712, the length of a second arrow 1722, and the length of a third arrow 1732, based on the first candidate arrow information corresponding to a first contour 1710, the second candidate arrow information corresponding to a second contour 1720, and the third candidate arrow information corresponding to a third contour 1730. The medical imaging device 100 may determine a higher score as the sum of the length of the first arrow 1712, the length of the second arrow 1722, and the length of the third arrow 1732 decreases.

Referring to FIG. 18, the medical imaging device 100 may determine the score based on a distance between intersection points 1851 and 1852 of two contours 1810 and 1820 included in the at least one contour 1810 and 1820, and on a distance between contact points 1812 and 1822 of the at least one contour 1810 and 1820 and the at least one arrow 1811 and 1821. In more detail, the medical imaging device 100 may determine a higher score as the distance between the intersection points 1851 and 1852 of two contours 1810 and 1820 included in the at least one contour 1810 and 1820, and the distance between the contact points 1812 and 1822 of the at least one contour 1810 and 1820 and the at least one arrows 1811 and 1821 increase.

The medical imaging device 100 may obtain the first arrow 1811 corresponding to the first contour 1810 included in the at least one contour based on the arrow information. In addition, the medical imaging device 100 may obtain the second arrow 1821 corresponding to the second contour 1820 included in the at least one contour based on the arrow information.

The medical imaging device 100 may obtain the first intersection point 1851 and the second intersection point 1852 of the first contour 1810 and the second contour 1820.

In addition, the medical imaging device 100 may determine, as the first contact point 1812, a point where the first contour 1810 and the first arrow 1811 are closest to each other. The first contact point 1812 may be a start point of the first arrow 1811. In addition, the first contact point 1812 may be a point on the first contour 1810, that is closest to the first arrow 1811.

In addition, the medical imaging device 100 may determine, as the second contact point 1822, a point where the second contour 1820 and the first arrow 1821 are closest to each other. The second contact point 1822 may be a start point of the second arrow 1821. In addition, the second contact point 1822 may be a point on the second contour 1820, that is closest to the second arrow 1821.

The medical imaging device 100 may determine a score based on a distance 1831 between the first intersection point 1851 and the first contact point 1812, a distance 1841 between the first intersection point 1851 and the second contact point 1822, a distance 1832 between the second intersection point 1852 and the first contact point 1812, and a distance 1842 between the second intersection point 1852 and the second contact point 1822. The medical imaging device 100 may determine a higher score as the sum of the distance 1831 between the first intersection point 1851 and the first contact point 1812, the distance 1841 between the first intersection point 1851 and the second contact point 1822, the distance 1832 between the second intersection point 1852 and the first contact point 1812, and the distance 1842 between the second intersection point 1852 and the second contact point 1822 increases.

Figure 19:
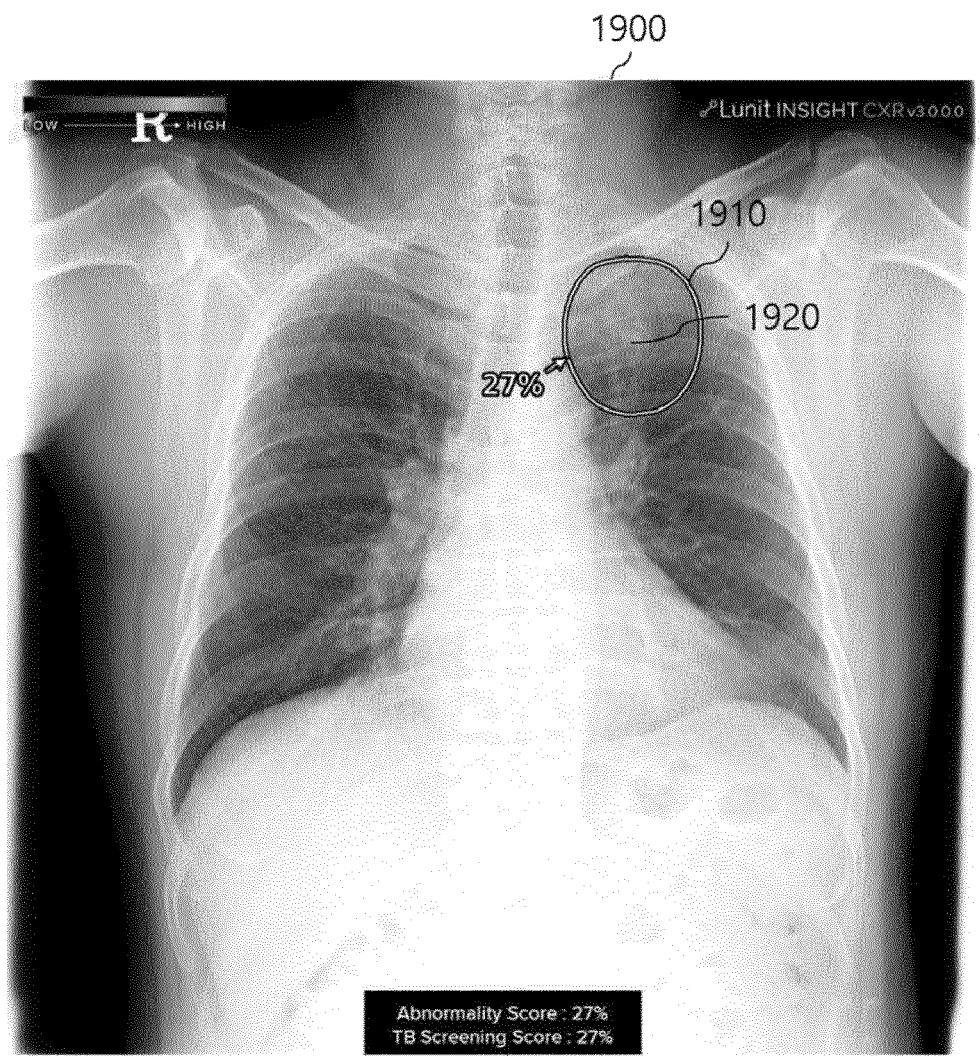
FIG. 19 illustrates a medical image.

FIG. 19 illustrates a medical image.

Similar to FIG. 2, the medical imaging device 100 may perform obtaining 210 lesion information on at least one lesion included in a medical image 1900. In addition, the medical imaging device 100 may perform generating a heat map 1920 corresponding to at least one lesion in the medical image based on the obtained lesion information.

The heat map 1920 may be displayed on the lesion region included in the lesion information. In addition, the heat map 1920 may be displayed to be greater than the lesion region included in the lesion information.

The medical imaging device 100 may display color and transparency differently based on the probability that the pixel of the medical image 1900 is included in the lesion region, so as to generate the heat map 1920. For example, as the probability that a pixel is included in the lesion region increases, it may be expressed in a red color scheme, and as the probability that a pixel is included in the lesion region decreases, it may be expressed in a blue color scheme. In addition, as the probability that the pixel is included in the lesion region increases, it may be expressed opaquely, and as the probability that the pixel is included in the lesion region decreases, it may be expressed transparently.

The medical imaging device 100 may obtain a maximum value of the probability that a pixel on the medical image 1900 is included in the lesion region. In addition, the medical imaging device 100 may obtain a maximum value of probability that a pixel on the medical image 1900 is included in the lesion region. In addition, the medical imaging device 100 may determine whether or not the maximum value of the probability is less than a threshold value. In this case, the threshold value may be a predetermined value. If the probability that the pixel is included in the lesion region is low, the heat map 1920 may have high transparency or may be expressed in an inconspicuous color, making it difficult for a medical practitioner to identify. For example, as illustrated in FIG. 19, if the probability that the pixel is included in the lesion region is low as 27%, it may be difficult for the medical practitioner to identify the heat map. The medical imaging device 100 may determine whether or not the maximum value of the probability is lower than a threshold value, so as to determine whether or not it is convenient for the medical practitioner to identify the heat map 1920.

If the maximum value of the probability is less than the threshold value, the medical imaging device 100 may perform generating a contour 1910 surrounding at least a portion of the heat map 1920. The contour 1910 may be smaller than or same as the heat map 1920. However, aspects are not limited thereto, and the contour 1910 may be larger than the heat map 1920. The medical imaging device 100 may generate a contour if it is difficult for the medical practitioner to identify the heat map 1920. If it is difficult for the medical practitioner to identify the heat map 1920, the medical imaging device 100 may display only the contour or simultaneously display the contour and the heat map, so that the medical practitioner can easily identify the lesion information displayed on the display.

The configuration for obtaining the probability that each pixel on the medical image 1900 is included in the lesion region has been described above. However, aspects are not limited thereto. The medical imaging device 100 may obtain probability that each unit region including at least one pixel is included in the lesion region. If the medical imaging device 100 uses the unit region, the same description may be applicable, and thus a redundant description will be omitted.

Figure 20:
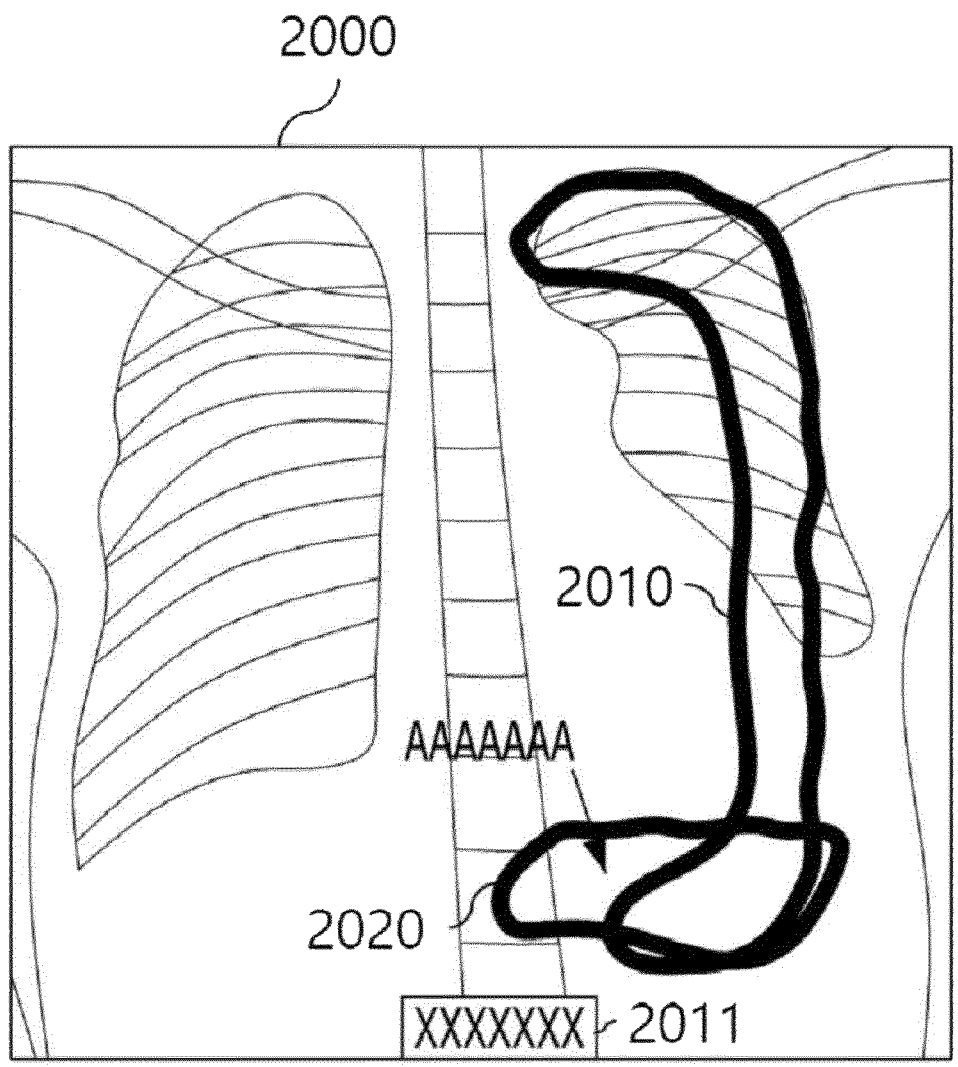
FIG. 20 illustrates a medical image.

FIG. 20 illustrates a medical image.

Similar to FIG. 2, the medical imaging device 100 may perform obtaining 210 lesion information on at least one lesion included in a medical image 2000. In addition, the medical imaging device 100 may perform generating (220) at least one contour corresponding to at least one lesion in the medical image, based on the obtained lesion information. In addition, similar to FIG. 9, the medical imaging device 100 may generate arrows and text. However, in certain circumstances, the medical imaging device 100 may not generate an arrow.

The medical imaging device 100 may determine whether or not the lesion region or the inner region of the contour is greater than a threshold value. If the lesion region or the inner region of the contour is greater than a threshold value, the medical imaging device 100 may not generate an arrow for the corresponding contour.

Alternatively, the medical imaging device 100 may determine whether or not a ratio of the lesion region or the inner region of the contour to the medical image is greater than a threshold value. If the ratio of the lesion region or the inner region of the contour to the medical image 2000 is greater than the threshold value, the medical imaging device 100 may not generate an arrow for the corresponding contour.

In addition, the medical imaging device 100 may not generate an arrow, if the type of lesion included in the lesion information is inevitably displayed in a large size on the medical image. Examples of such lesions may include mediastinal widening (MW) or cardiomegaly (Cm).

If an arrow is not generated, the medical imaging device 100 may display text related to lesion information on a partial region of the medical image 2000. For example, text related to the lesion information may be displayed at the bottom or corner of the medical image 2000.

Referring to FIG. 20, since a contour 2020 is a relatively small region, arrows and text may be displayed. However, since a contour 2010 is a relatively large region, a text 2011 may be displayed, but an arrow may not be displayed. The medical imaging device 100 may display the text 2011 for the contour 2010 in a partial region or partial position of the medical image 2000. For example, the medical imaging device 100 may display the text 2011 for the contour 2010 at a corner or bottom of the medical image 2000.

In order to indicate that there is a correlation between the contour 2010 and the text 2011, the medical imaging device 100 may display the shape of the line of the contour 2010 in front of the text 2011. In addition, the medical imaging device 100 may set the color of the contour 2010 and the color of the text 2011 to be the same.

Figure 21:
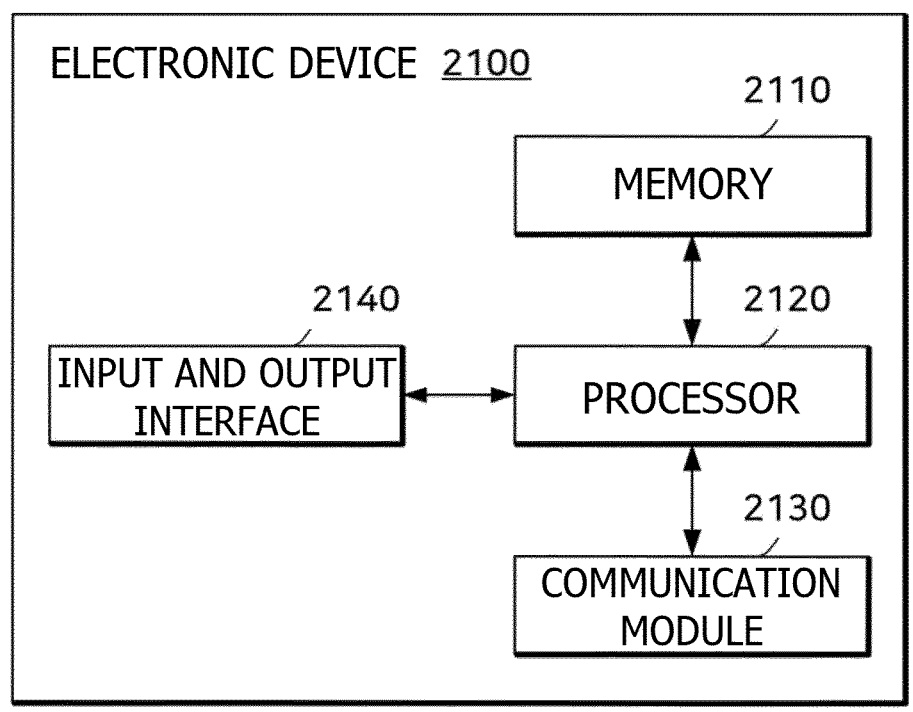
FIG. 21 is a block diagram of an internal configuration of an electronic device.

FIG. 21 is a block diagram of an internal configuration of an electronic device 2100. The electronic device 2100 may include a memory 2110, a processor 2120, a communication module 2130, and an input and output interface 2140. For example, the electronic device 2100 may include the medical imaging device 100 described above. As illustrated in FIG. 21, the electronic device 2100 may be configured to communicate information and/or data through a network by using the communication module 2130.

The memory 2110 may include any non-transitory computer-readable recording medium. The memory 2110 may include a permanent mass storage device such as random access memory (RAM), read only memory (ROM), disk drive, solid state drive (SSD), flash memory, and so on. As another example, a non-destructive mass storage device such as ROM, SSD, flash memory, disk drive, and the like may be included in the electronic device 2100 as a separate permanent storage device that is separate from the memory. In addition, the memory 2110 may be stored with the operating system and at least one program code (e.g., codes for obtaining lesion information installed and driven in the electronic device 2100, determining the shape and position of a contour, determining the position of a text region, and the like).

These software components may be loaded from a computer-readable recording medium separate from the memory 2110. Such a separate computer-readable recording medium may include a recording medium directly connectable to the electronic device 2100, and may include a computer-readable recording medium such as a floppy drive, a disk, a tape, a DVD/CD-ROM drive, a memory card, and the like, for example. In another example, the software components may be loaded into the memory 2110 through the communication module 2130 rather than the computer-readable recording medium. For example, at least one program may be loaded into the memory 2110 based on a computer program (e.g., a program for determining the shape and position of a contour, positioning a text region, creating an arrow, positioning an arrow, and the like) installed by the files provided by the developers, or by a file distribution system that distributes an installation file of an application through the communication module 2130.

The processor 2120 may be configured to process the commands of the computer program by performing basic arithmetic, logic, and input and output operations. The commands may be provided to a user terminal (not illustrated) or another external system by the memory 2110 or the communication module 2130. For example, the processor 2120 may receive a medical image and obtain lesion information on at least one lesion detected from the medical image. In addition, the processor 2120 may determine shape and position of at least one contour corresponding to the at least one lesion based on the obtained lesion information, and determine a position of at least one text region that includes a text indicating the lesion information on the at least one lesion in the medical image. In this case, the processor 2120 may provide the determined shape and position of the contour, the position of the text region, and the like to the input and output interface 2140, the user terminal (not illustrated), and/or another external system.

The communication module 2130 may provide a configuration or function for the user terminal (not illustrated) and the electronic device 2100 to communicate with each other through a network, and may provide a configuration or function for the electronic device 2100 to communicate with an external system (e.g., a separate cloud system). For example, control signals, commands, data, and the like provided under the control of the processor 2120 of the electronic device 2100 may be transmitted to the user terminal and/or the external system through the communication module 2130 and the network through the communication module of the user terminal and/or external system. For example, the user terminal and/or the external system may receive the medical image, the shape and position of the contour, content of text, the position of text region, and the like received from the electronic device 2100.

In addition, the input and output interface 2140 of the electronic device 2100 may serve as a means for interfacing with a device (not illustrated) for input or output which may be connected to or included in the electronic device 2100. For example, the input and output interface 2140 may include means for interfacing with a display configured to display a medical image. In FIG. 21, the input and output interface 2140 is illustrated as a component configured separately from the processor 2120, but aspects are not limited thereto, and the input and output interface 2140 may be configured to be included in the processor 2120. The electronic device 2100 may include more components than those illustrated in FIG. 21. Meanwhile, most of the related components may not necessarily require exact illustration.

The processor 2120 of the electronic device 2100 may be configured to manage, process, and/or store the information and/or data received from a plurality of user terminals and/or a plurality of external systems. The processor 2120 may obtain lesion information on at least one lesion detected from the medical image, and determine the shape and position of at least one contour corresponding to the at least one lesion based on the obtained lesion information. In addition, the processor 2120 may determine a position of at least one text region that includes a text indicating the lesion information on the at least one lesion in the medical image, and display the at least one contour and the text included in the at least one text region on the medical image, based on the determined shape and position of the at least one contour and the determined position of the at least one text region.

Figure 22:
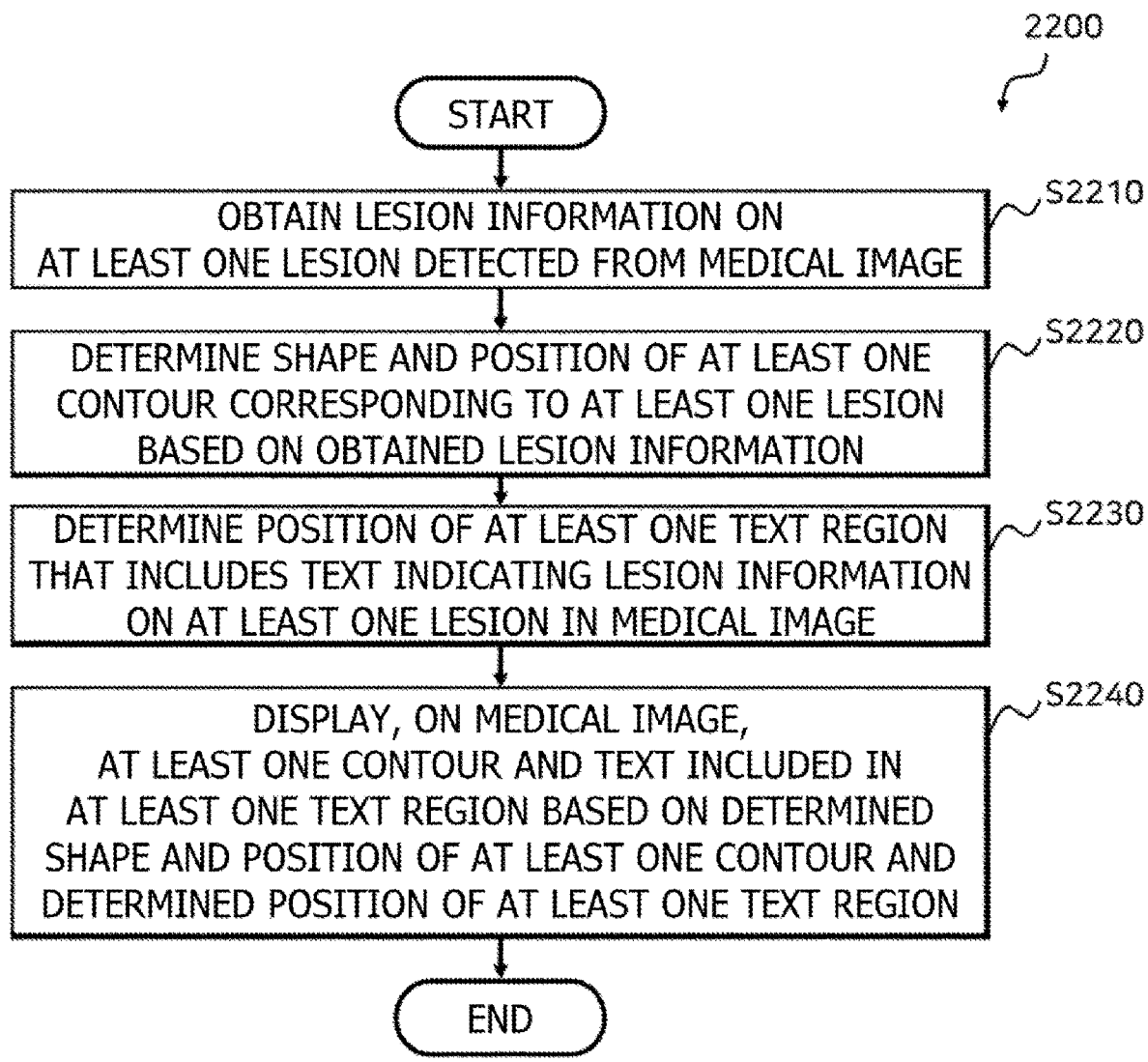
FIG. 22 is a flowchart illustrating a method for operating a medical imaging device.

FIG. 22 is a flowchart illustrating a method 2200 for operating the medical imaging device. The method 2200 for operating the medical imaging device may be performed by a processor (e.g., at least one processor of a medical imaging device (electronic device) or the like). As illustrated, the method 2200 for operating the medical imaging device may be started by the processor obtaining lesion information on at least one lesion detected from the medical image, at S2210. Additionally or alternatively, the processor may obtain lesion information on a plurality of lesions detected from the medical image.

The processor may determine the shape and position of at least one contour corresponding to the at least one lesion based on the obtained lesion information, at S2220. For example, the processor may determine some of the plurality of lesions to be displayed on the medical image, and determine the shape and position of at least one contour of the determined some lesions. In addition, the processor may determine a position of at least one text region that includes a text indicating the lesion information on at least one lesion in the medical image, at S2230. For example, the processor may determine the position of the at least one text region based on at least one of: a distance between the at least one contour and the at least one text region; or presence of overlap between the at least one contour and the at least one text region. In addition, the processor may determine a position of at least one text including lesion information on the determined some lesions. In addition, the at least one text region may include a plurality of text regions, and in this case, the processor may determine a position of each of the plurality of text regions based on a distance between the plurality of text regions.

The processor may display the at least one contour and the text included in the at least one text region on the medical image, based on the determined shape and position of the at least one contour and the determined position of the at least one text region, at S2240. In addition, the processor may generate at least one arrow pointing to the at least one contour, and display the at least one arrow generated to connect between the at least one contour and the at least one text region on the medical image. In this case, the processor may obtain lesion information on a plurality of lesions detected from the medical image, and generate arrows for each of the plurality of lesions. Then, the processor may display arrows for each of the plurality of lesions on the medical image such that the generated arrows for each of the plurality of lesions do not cross each other. Additionally or alternatively, the processor may display the arrow for each of the plurality of lesions on the medical image such that the generated arrow for each of the plurality of lesions does not cross the contour corresponding to each of the plurality of lesions. Additionally or alternatively, at least one contact region contacting the at least one contour may be determined, and the generated at least one arrow may be displayed to be connected to the at least one contact region. For example, the at least one contact region may include a plurality of contact regions contacting the at least one contour, in which case the processor may determine the at least one contact region based on a distance between the plurality of contact regions.

The processor may determine some of the plurality of lesions to be displayed on the medical image. In this case, the processor may identify any of the plurality of lesions that has overlapping lesion regions, and determine some of the plurality of lesions based on at least one of: a size of the overlapping region between overlapping lesions; probability that each of the overlapping lesions is a lesion; relevance between overlapping lesions; or probability of presence of some of the overlapping lesions in one medical image. According to this example, a medical practitioner can intensively observe around the contour, which is a part of the medical image, and finally can easily determine whether or not a lesion is present inside the contour.

The present disclosure has been mainly described above with respect to the examples thereof. Those of ordinary skill in the art to which the present disclosure pertains will understand that the present disclosure can be implemented in a modified form without departing from the essential characteristics of the present disclosure. Therefore, the disclosed examples should be considered in an illustrative rather than a restrictive sense. The scope of the present disclosure should be construed by the claims rather than the foregoing description, and all differences within the scope equivalent thereto should be construed to be included in the present disclosure.

Meanwhile, the examples described above can be written as a program that can be executed on a computer, and can be implemented in a general-purpose digital computer that operates the program using a computer-readable recording medium. The computer-readable recording medium includes a storage medium such as a magnetic storage medium (e.g., a ROM, a floppy disk, a hard disk, and the like) and an optically readable medium (e.g., a CD-ROM, a DVD, and the like).

What is claimed is:

1. A method for operating a medical imaging device comprising:
    obtaining lesion information on a plurality of lesions detected from a medical image;
    determining shapes and positions of a plurality of contours corresponding to the plurality of lesions based on the obtained lesion information;
    determining positions of a plurality of text regions, to be displayed together with the plurality of lesions in the medical image, comprising separate text boxes indicating the lesion information on the plurality of lesions in the medical image based on at least one of: at least one distance between the plurality of text regions, a presence of overlap between the plurality of text regions, or distances between the plurality of contours and the plurality of text regions, in a way that understandability of the plurality of contours is improved by at least one of: avoiding overlapping between the plurality of text regions, avoiding the overlapping between the plurality of text regions and the plurality of lesions, displaying the plurality of text regions and the plurality of lesions in proximity based on relevancy, or positioning arrows to point the plurality of text regions to relevant lesions of the plurality of lesions; and determining arrow position information of at least one arrows by having a start point or an end point, of any arrow of the at least one arrows, based on an intersection point, of any two contours of the plurality of contours, and a contact point, of the any arrow of the at least one arrows and any one contour of the any two contours;

simultaneously displaying the plurality of contours and the text in the plurality of text regions on the medical image and the determined arrow position information of the at least one arrows, based on the determined shapes and the determined positions of the plurality of contours and the determined shapes and the determined positions of the determined positions of the plurality of text regions.

2. The method according to claim 1, wherein:
the determining the shapes and the positions of the plurality of contours comprises:
  determining some of the plurality of lesions to be displayed on the medical image; and
  determining a shapes and a positions of contours for the determined some lesions; and
the determining the positions of the plurality of text regions comprises determining positions of the plurality of text regions comprising the lesion information on the determined some lesions.

3. The method according to claim 2, wherein the determining the some lesions comprising:
identifying any of the plurality of lesions that has an overlapping lesion region; and
determining some of the plurality of lesions based on at least one of: a size of an overlapping region between overlapping lesions; probability that each of the overlapping lesions is a lesion; relevance between the overlapping lesions; or probability of presence of some of the overlapping lesions in one medical image.

4. The method according to claim 1, further comprising:
generating a plurality of arrows pointing to the plurality of contours,
wherein the displaying comprises displaying the generated plurality of arrows on the medical image to connect the plurality of contours and the plurality of text regions.

5. The method according to claim 4, wherein:
the generating the plurality of arrows comprises generating an arrow for each of the plurality of lesions; and
the displaying the generated plurality of arrows on the medical image comprises displaying the arrows for each of the plurality of lesions on the medical image with the generated arrows for each of the plurality of lesions not crossing each other.

6. The method according to claim 4, wherein:
the generating the plurality of arrows comprises generating an arrow for each of the plurality of lesions; and
the displaying the generated plurality of arrows on the medical image comprises displaying the arrows for each of the plurality of lesions on the medical image with the generated arrows for each of the plurality of lesions not crossing a contour corresponding to each of the plurality of lesions.

7. The method according to claim 4, wherein the displaying the generated plurality of arrows on the medical image comprises:
determining a plurality of contact regions in which the generated plurality of arrows is in contact with the plurality of contours; and
displaying the generated plurality of arrows as being connected to the plurality of contact regions.

8. The method according to claim 7, wherein the determining the plurality of contact regions comprises determining, from the plurality of contact regions contacting the plurality of contours the plurality of contact regions based on at least one distance between the plurality of contact regions.

9. An electronic device comprising:
a memory storing one or more instructions; and
at least one processor configured to execute the stored one or more instructions to:
  obtain lesion information on a plurality of lesions detected from a medical image;
  determine shapes and positions of a plurality of contours corresponding to the plurality of lesions based on the obtained lesion information;
  determine positions of plurality of text regions, to be displayed together with the plurality of lesions in the medical image, that comprise separate text boxes indicating the lesion information on the plurality of lesions in the medical image based on at least one of: at least one distance between the plurality of text regions, a presence of overlap between the plurality of text regions, or distances between the plurality of contours and the plurality of text regions, in a way that understandability of the plurality of contours is improved by at least one of: avoiding overlapping between the plurality of text regions, avoiding the overlapping between the plurality of text regions and the plurality of lesions, displaying the plurality of text regions and the plurality of lesions in closeness based on their relevancy, or positioning arrows to point the text regions to relevant lesions of the plurality of lesions; and
  determine arrow positions of at least one arrows by having a start point or an end point, of any arrow of the at least one arrows, based on an intersection point, of any two contours of the plurality of contours, and a contact point, of the any arrow of the at least one arrows and any one contour of the any two contours;
  simultaneously display the plurality of contours and the text in the plurality of text regions on the medical image and the determined arrow position information of the at least one arrows, based on the determined shapes and the determined positions of the a plurality of contours and the determined shapes and the determined positions of the plurality of text regions.

10. The electronic device according to claim 9, wherein the at least one processor is further configured to:

determine some of the plurality of lesions to be displayed on the medical image;

determine the shapes and the positions of the contours for the determined some lesions; and determine a position of at least one text region comprising the lesion information on the determined some lesions.

11. The electronic device according to claim 10, wherein the at least one processor is further configured to:

identify any of the plurality of lesions that has an overlapping lesion region; and determine some of the plurality of lesions based on at least one of: a size of an overlapping region between overlapping lesions; probability that each of the overlapping lesions is a lesion; relevance between the overlapping lesions; or probability of presence of some of the overlapping lesions in one medical image.

12. The electronic device according to claim 9, wherein the at least one processor is further configured to:

generate a plurality of arrows pointing to the plurality of contours; and display the generated plurality of arrows on the medical image to connect the plurality of contours and the plurality of text regions.

13. The electronic device according to claim 12, wherein the at least one processor is further configured to:

generate the plurality of arrows for the plurality of lesions; and display the plurality of arrows for each of the plurality of lesions on the medical image with the generated arrows for each of the plurality of lesions not crossing each other.

14. The electronic device according to claim 12, wherein the at least one processor is further configured to:

generate the plurality of arrows for the plurality of lesions; and display the plurality of arrows for each of the plurality of lesions on the medical image with the generated arrows for each of the plurality of lesions not crossing a contour corresponding to each of the plurality of lesions.

15. The electronic device according to claim 12, wherein the at least one processor is further configured to:

determine a plurality of contact regions in which the generated is plurality of arrows are in contact with the plurality of contours; and display the generated plurality of arrows as being connected to the plurality of contact regions.

16. The electronic device according to claim 15, wherein the at least one processor is further configured to:

determine, from the plurality of contact regions contacting the plurality of contours, the plurality of contact regions based on at least one distance between the plurality of contact regions.

* * * * *